United States Patent
Chalvignac et al.

(10) Patent No.: US 9,923,442 B2
(45) Date of Patent: Mar. 20, 2018

(54) BREATHING ASSISTANCE DEVICE WITH LINEAR ACTUATED GAS REGULATING VALVE

(75) Inventors: Philippe Auguste Chalvignac, Bella Vista (AU); Nan Hai Wu, Bella Vista (AU); Ken Taylor, Bella Vista (AU); Daniel Robert Judson, Bella Vista (AU); Paul Jan Klasek, Bella Vista (AU); Christopher Kingsley Blunsden, Bella Vista (AU)

(73) Assignee: RESMED LIMITED, Bella Vista (AU)

(*) Notice: Subject to any disclaimer, the term of this patent is extended or adjusted under 35 U.S.C. 154(b) by 968 days.

(21) Appl. No.: 13/377,244

(22) PCT Filed: Jun. 9, 2010

(86) PCT No.: PCT/AU2010/000708
§ 371 (c)(1),
(2), (4) Date: Dec. 9, 2011

(87) PCT Pub. No.: WO2010/141983
PCT Pub. Date: Dec. 16, 2010

(65) Prior Publication Data
US 2012/0085348 A1    Apr. 12, 2012

Related U.S. Application Data

(60) Provisional application No. 61/185,250, filed on Jun. 9, 2009.

(51) Int. Cl.
*A62B 9/02* (2006.01)
*H02K 33/18* (2006.01)
(Continued)

(52) U.S. Cl.
CPC ......... *H02K 33/18* (2013.01); *A61M 16/0006* (2014.02); *A61M 16/0866* (2014.02);
(Continued)

(58) Field of Classification Search
CPC .............. A61M 16/201; A61M 16/202; A61M 16/203; A61M 16/204; A61M 16/205;
(Continued)

(56) References Cited

U.S. PATENT DOCUMENTS 2,922,932 A * 1/1960 Glowacki et al. ............ 335/299
2,944,235 A * 7/1960 Peters ........................... 336/199
(Continued)

FOREIGN PATENT DOCUMENTS

DE       8 809 143      12/1989
DE       10 114 628      9/2002
(Continued)

OTHER PUBLICATIONS

International Preliminary Report on Patentability and Written Opinion for corresponding PCT Application No. PCT/AU2010/000708, dated Dec. 12, 2011, 18 pages.
(Continued)

Primary Examiner — Peter S Vasat
(74) Attorney, Agent, or Firm — Nixon & Vanderhye, P.C.

(57) ABSTRACT

A breathing assistance device includes a gas regulating valve (1300). The gas regulating valve is operated by a linear actuator (1330). The linear actuator may include a movable member that moves an obstruction member between an open position and a closed position. The linear actuator is isolated from a gas flow path through the valve.

44 Claims, 25 Drawing Sheets

(51) Int. Cl.
*A61M 16/20* (2006.01)
*F16K 31/06* (2006.01)
*F16K 31/08* (2006.01)
*H01F 5/02* (2006.01)
*H02K 5/22* (2006.01)
*H02K 7/14* (2006.01)
*A61M 16/10* (2006.01)
*A61M 16/08* (2006.01)
*H01F 5/04* (2006.01)
*H01F 7/06* (2006.01)
*A61M 16/00* (2006.01)
*A61M 16/06* (2006.01)
*A61M 16/12* (2006.01)
*A61M 16/16* (2006.01)
*A61M 39/22* (2006.01)

(52) U.S. Cl.
CPC ........ *A61M 16/1095* (2014.02); *A61M 16/20* (2013.01); *A61M 16/204* (2014.02); *A61M 16/205* (2014.02); *A61M 16/206* (2014.02); *A61M 16/209* (2014.02); *F16K 31/0651* (2013.01); *F16K 31/0693* (2013.01); *F16K 31/082* (2013.01); *F16K 31/084* (2013.01); *H01F 5/02* (2013.01); *H01F 5/04* (2013.01); *H01F 7/066* (2013.01); *H02K 5/225* (2013.01); *H02K 7/14* (2013.01); *A61M 16/0066* (2013.01); *A61M 16/06* (2013.01); *A61M 16/12* (2013.01); *A61M 16/16* (2013.01); *A61M 39/22* (2013.01); *A61M 2016/0027* (2013.01); *A61M 2016/0036* (2013.01); *A61M 2016/0042* (2013.01); *A61M 2202/0208* (2013.01); *A61M 2205/8206* (2013.01); *A61M 2209/06* (2013.01); *Y10T 29/4902* (2015.01); *Y10T 29/49412* (2015.01)

(58) Field of Classification Search
CPC .......... A61M 2016/0036; A61M 16/20; A61M 16/206; A61M 39/22; F16K 31/0651
USPC ................ 251/129.21; 137/872; 128/201.28, 128/205.24, 206.14, 207.16, 204.21 128/204.18
See application file for complete search history.

(56) References Cited

U.S. PATENT DOCUMENTS

| 3,606,241 | A | | 9/1971 | Bornholdt |
| 4,196,886 | A | * | 4/1980 | Murray ........................ 251/357 |
| 4,286,767 | A | | 9/1981 | Hashimoto et al. |
| 4,294,286 | A | | 10/1981 | Ohumi et al. |
| 4,437,645 | A | | 3/1984 | Nomura et al. |
| 4,530,374 | A | | 7/1985 | Akagi et al. |
| 4,531,708 | A | | 7/1985 | Livet |
| 4,720,646 | A | | 1/1988 | Torimoto |
| 4,890,815 | A | | 1/1990 | Hascher-Reichi et al. |
| 4,917,150 | A | | 4/1990 | Koch et al. |
| 5,056,556 | A | | 10/1991 | Nishimoto et al. |
| 5,540,220 | A | | 7/1996 | Gropper et al. |
| 5,758,863 | A | | 6/1998 | Buffet et al. |
| 6,644,316 | B2 | | 11/2003 | Bowman et al. |
| 6,994,308 | B1 | * | 2/2006 | Wang et al. ................ 251/30.04 |
| 7,000,612 | B2 | * | 2/2006 | Jafari et al. .............. 128/204.21 |
| 8,464,714 | B2 | * | 6/2013 | Chalvignac .............. 128/204.26 |
| 8,544,464 | B2 | * | 10/2013 | Chalvignac .............. 128/201.28 |
| 2002/0029004 | A1 | * | 3/2002 | Starr ...................... A61B 5/087 600/538 |
| 2003/0140907 | A1 | * | 7/2003 | Gagnon .............. F16K 31/0624 123/568.26 |
| 2004/0007232 | A1 | | 1/2004 | Rochat |
| 2004/0069305 | A1 | | 4/2004 | Niemela |
| 2005/0254680 | A1 | | 11/2005 | Kitamura |
| 2006/0186977 | A1 | | 8/2006 | Ito |
| 2007/0272890 | A1 | * | 11/2007 | Kopecek et al. .......... 251/129.1 |
| 2007/0283960 | A1 | | 12/2007 | Meckes et al. |
| 2008/0186601 | A1 | | 8/2008 | Honma |
| 2009/0223520 | A1 | * | 9/2009 | McAuley et al. ....... 128/205.25 |
| 2009/0314294 | A1 | * | 12/2009 | Chalvignac ....... A61M 16/0057 128/204.23 |

FOREIGN PATENT DOCUMENTS

| GB | 1 366 499 | | 9/1974 |
| GB | 2 439 839 | | 1/2008 |
| JP | H11 55925 A | | 2/1999 |
| JP | 2002-504408 A | | 2/2002 |
| JP | 2002-108456 | | 4/2002 |
| JP | 2004-512065 | | 4/2004 |
| JP | 2004-516115 | | 6/2004 |
| JP | 2004-519626 | | 7/2004 |
| JP | 3 675950 B2 | | 7/2005 |
| JP | 2008-539841 | | 11/2008 |
| WO | WO 1997/041812 | | 11/1997 |
| WO | WO 2000/032261 | | 6/2000 |
| WO | WO 2000/043060 | | 7/2000 |
| WO | WO 2002/068850 | | 9/2002 |
| WO | WO 2006/117379 | | 11/2006 |
| WO | WO2006117591 A1 * | | 11/2006 |
| WO | WO 2006117591 A1 * | | 11/2006 |
| WO | 2007/121230 A3 | | 10/2007 |
| WO | WO 2008/028228 | | 3/2008 |

OTHER PUBLICATIONS

Notice of Reasons for Rejection issued in Japanese Application No. 2012-514290 dated Aug. 19, 2014 (with translation).
Japanese Patent Office, "Decision of Rejection," (5 pages) issued in connection with Japanese Patent Application No. 2012-514290, dated May 18, 2015, along with its English language Translation (4 pages).
First Office Action (Notice of Reasons for Rejection) issued in related Japanese Application No. 2015-182732 dated Jul. 27, 2016 with English translation, 10 pages.
Japanese Office Action dated Mar. 27, 2017 in Japanese Application No. P2015-182732, with English translation (8 pages).
International Search Report issued in PCT/AU2010/000708, dated Oct. 19, 2010.
Written Opinion of the International Searching Authority for PCT/AU2010/000708, dated Oct. 19, 2010.
Extended Search Report issued in related European Application No. 10 78 5591.8, dated Nov. 20, 2017, (5 pages).

* cited by examiner

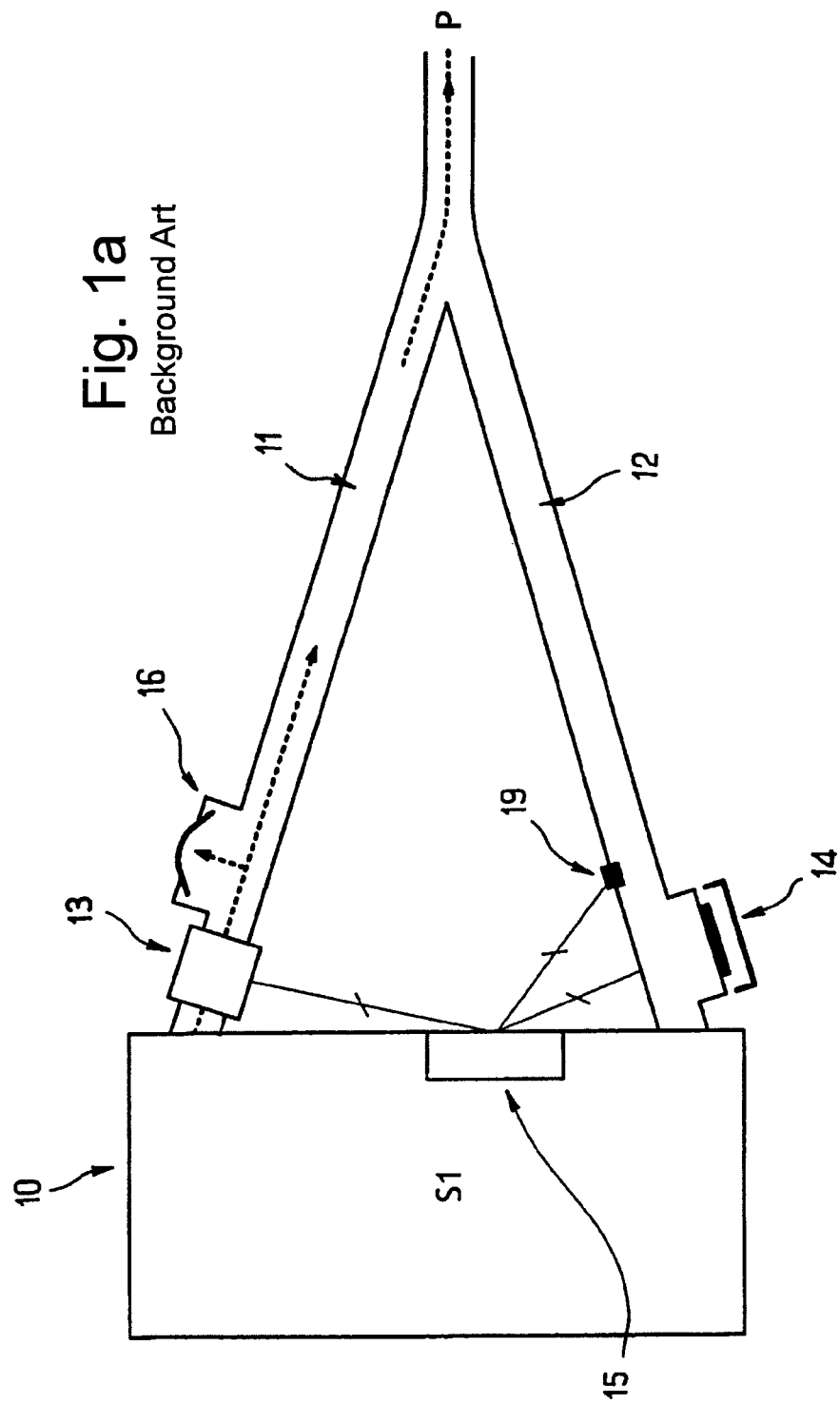

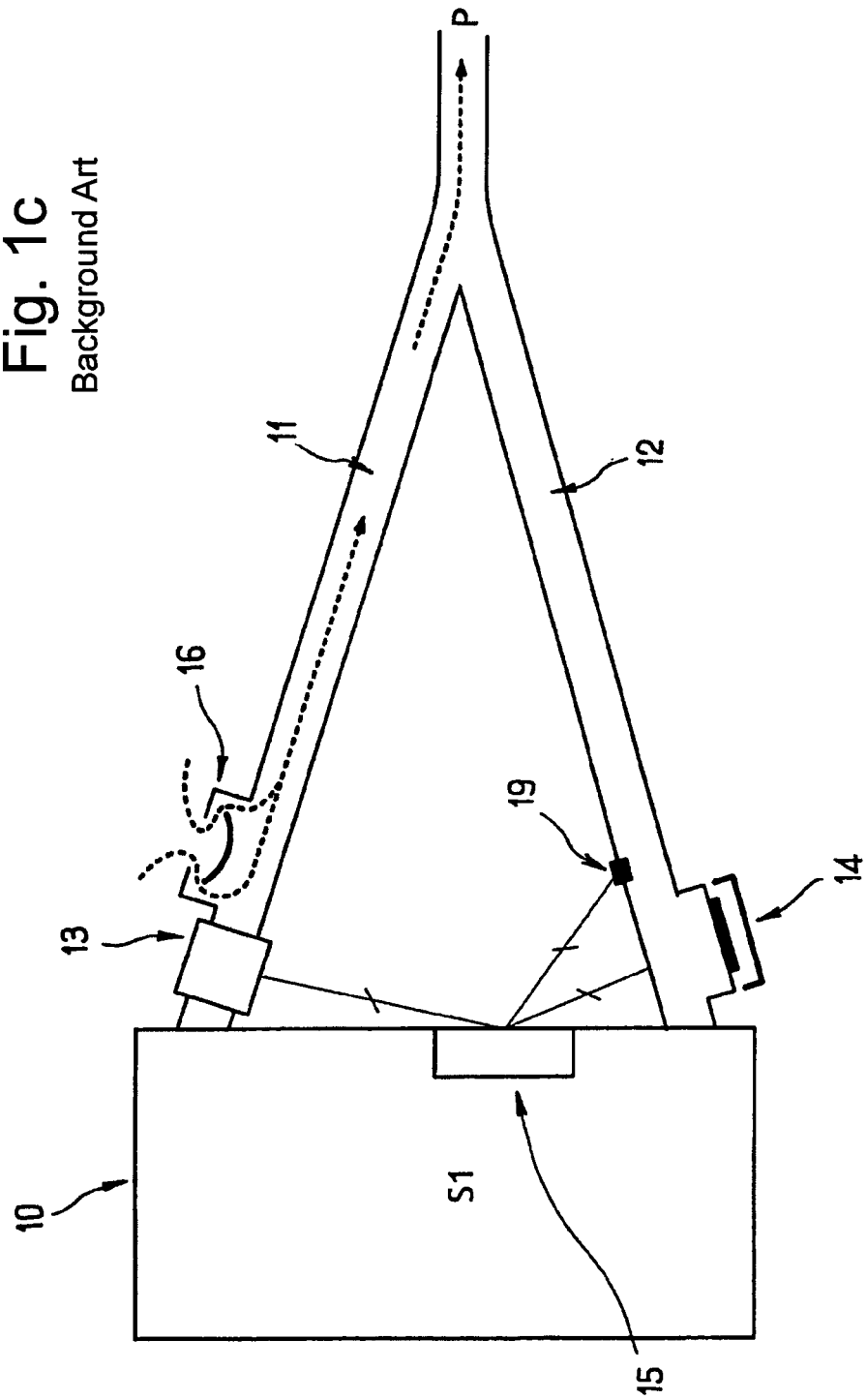

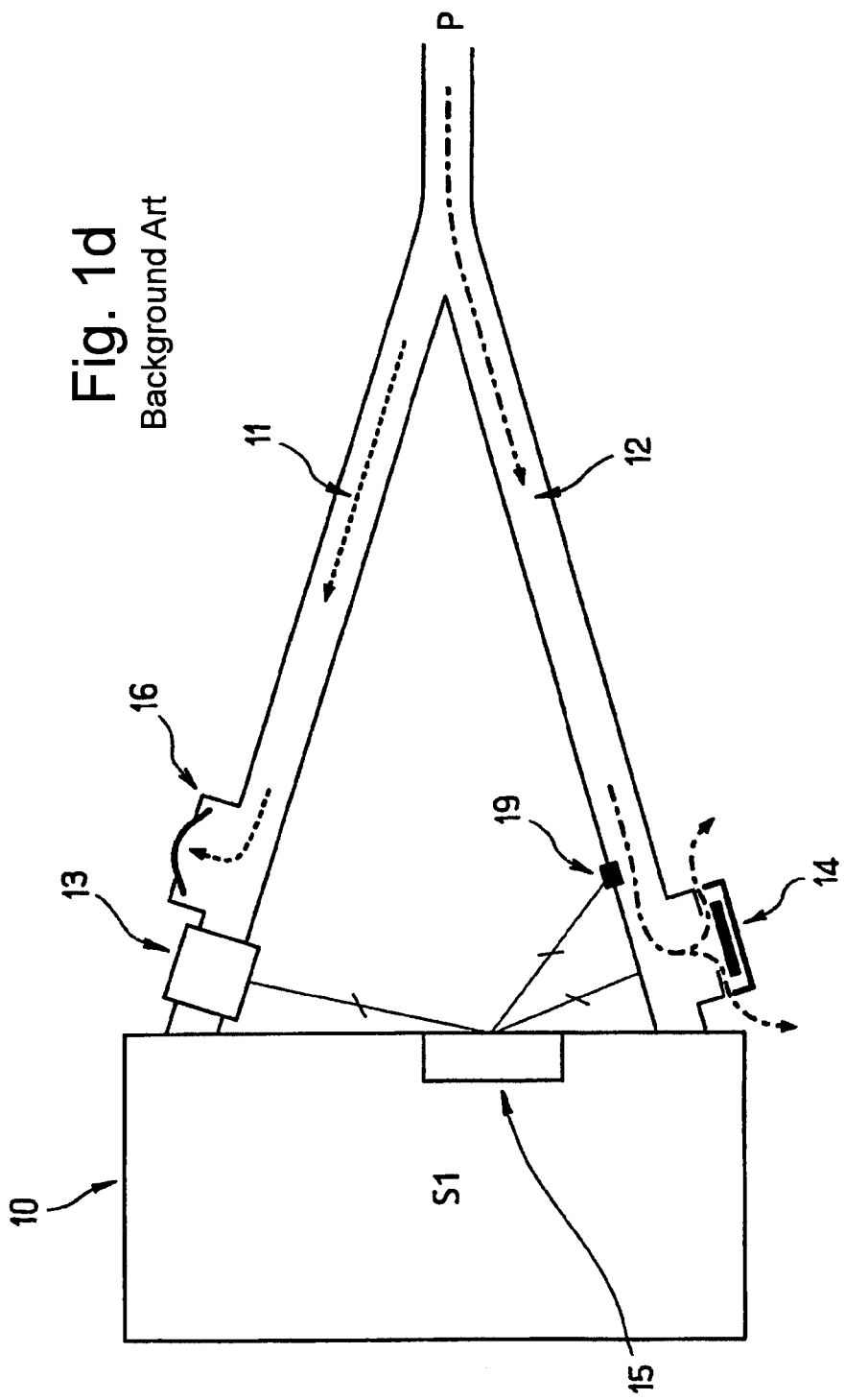

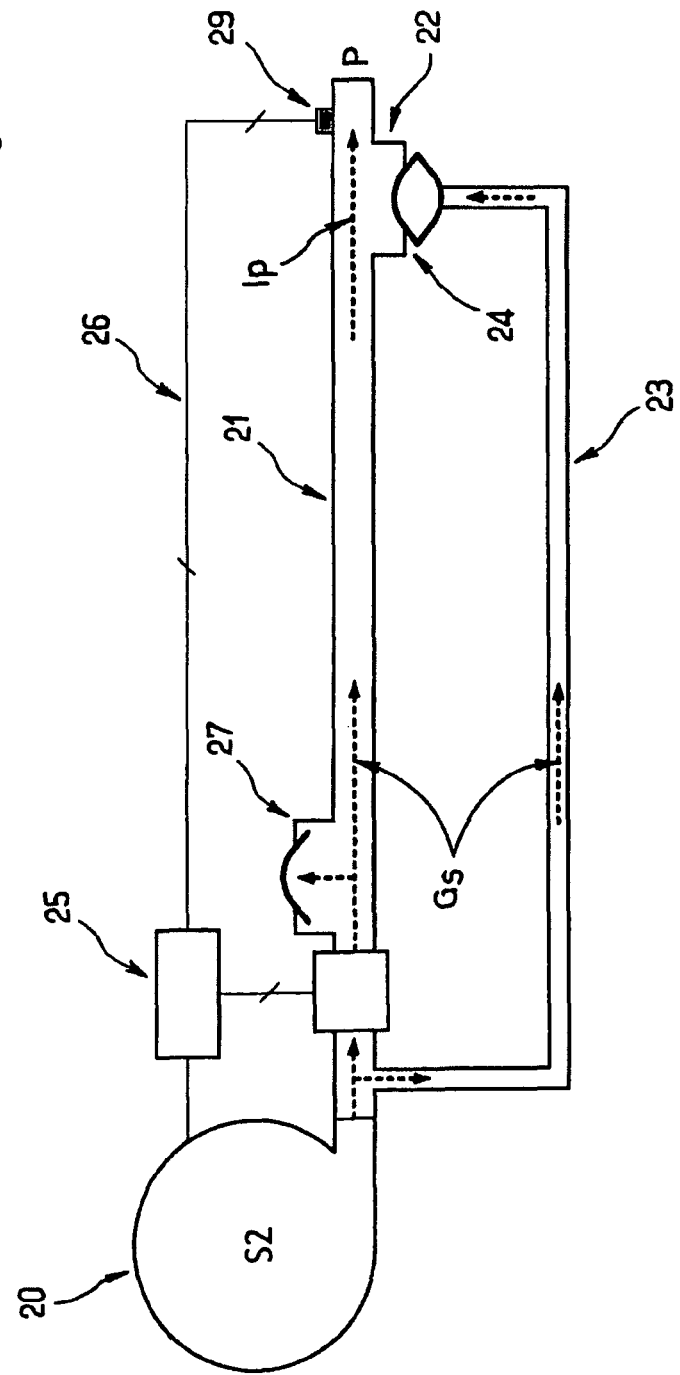

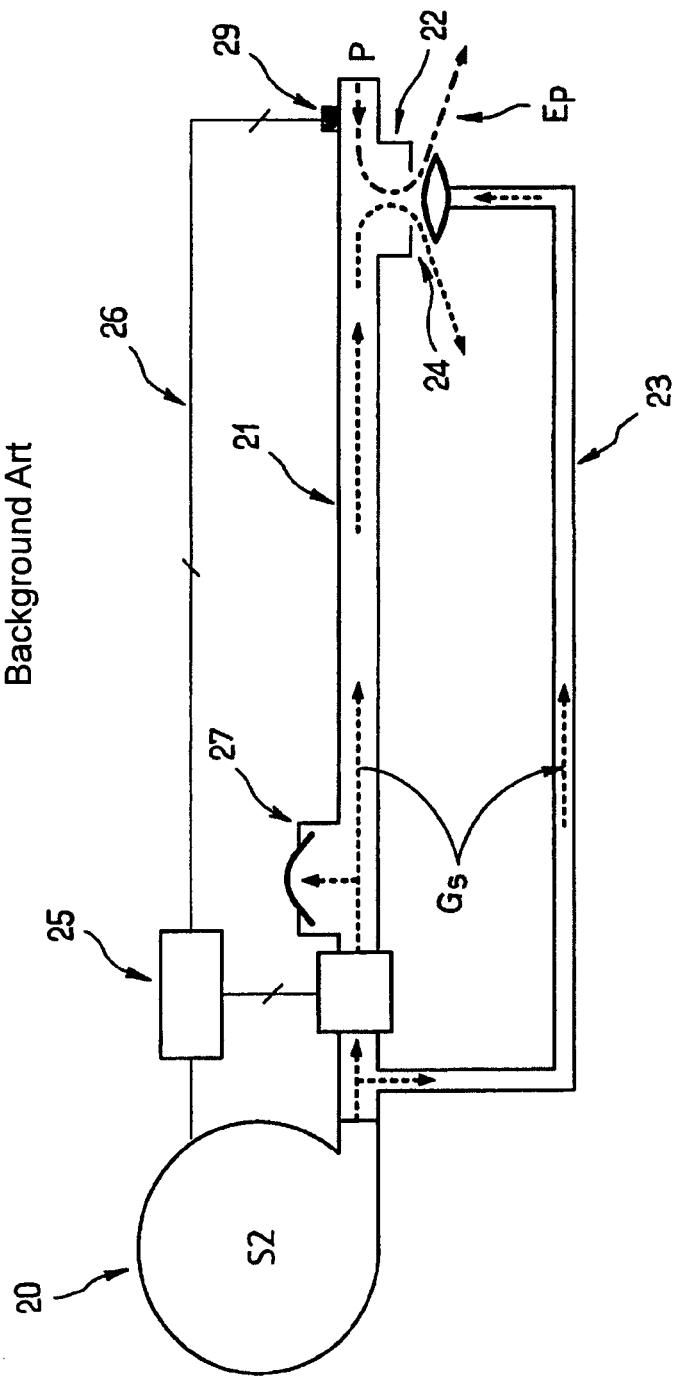

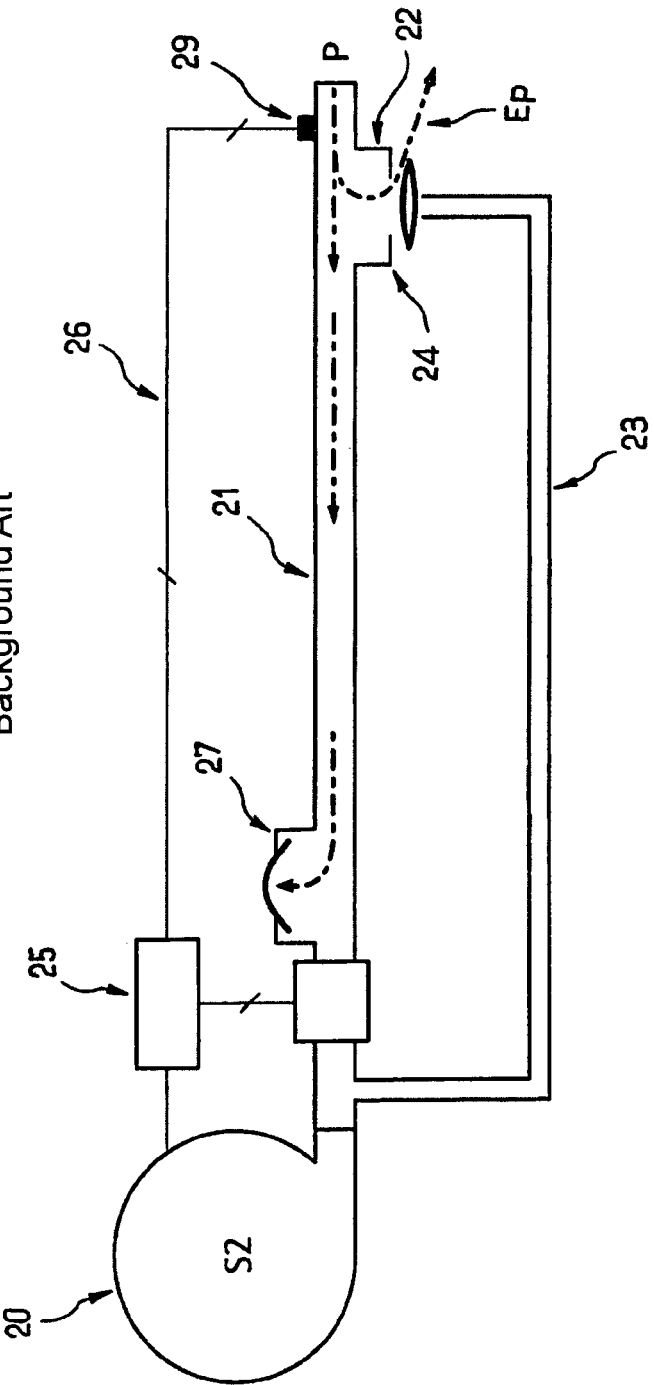

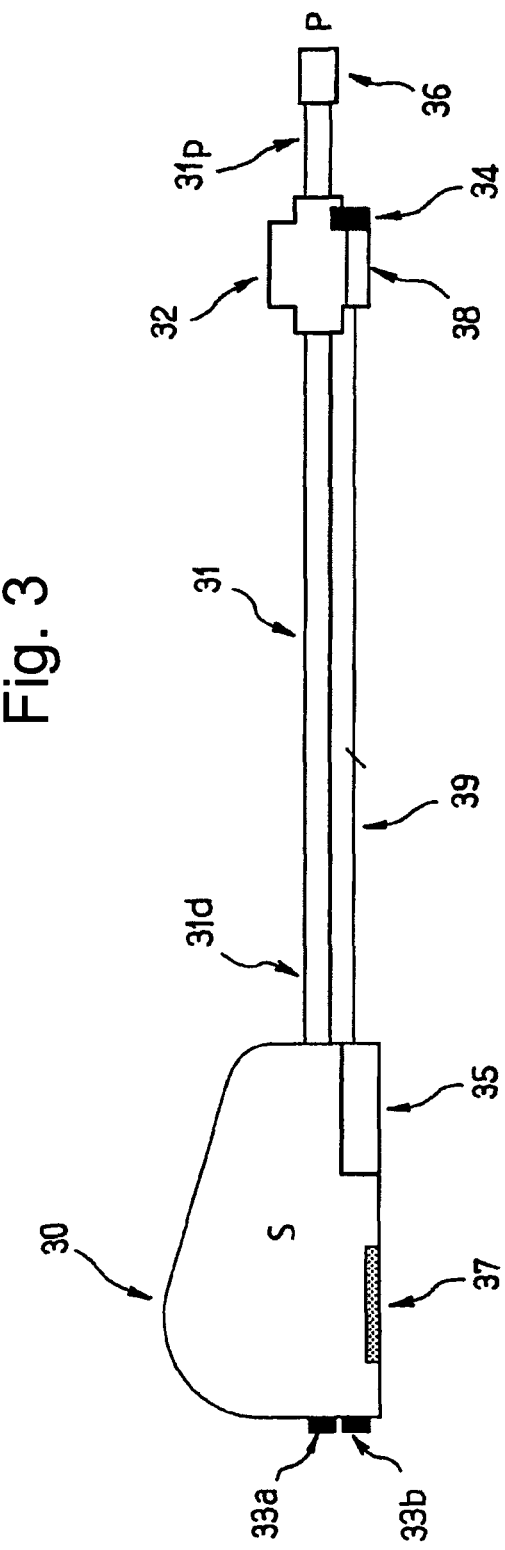

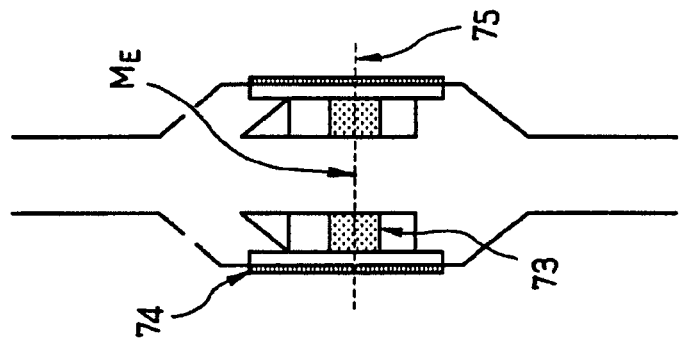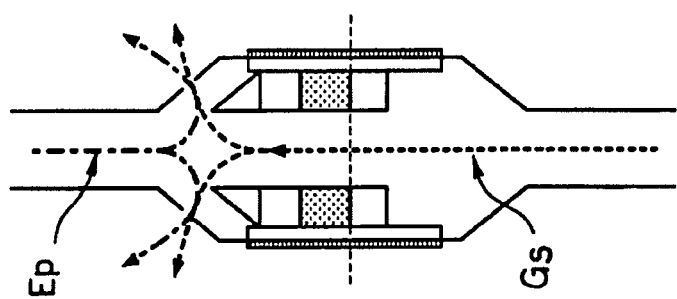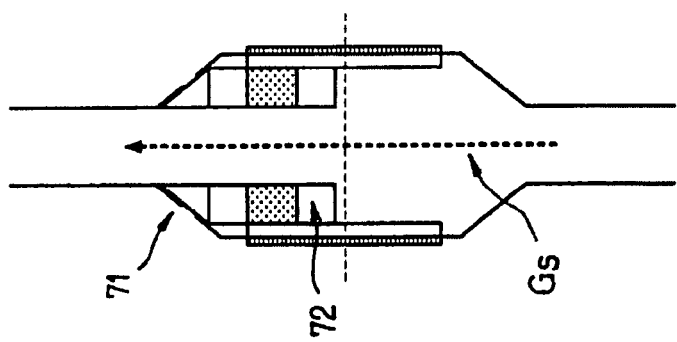

BREATHING ASSISTANCE DEVICE WITH LINEAR ACTUATED GAS REGULATING VALVE

CROSS REFERENCE TO RELATED APPLICATIONS

This application is the U.S. national phase of International Application No. PCT/AU2010/000708, filed Jun. 9, 2010, which designated the U.S. and claims the benefits of U.S. Provisional Patent Application Ser. No. 61/185,250, filed Jun. 9, 2009, the entire contents of each of which are incorporated herein by reference.

FIELD OF THE INVENTION

The present invention relates to a breathing assistance device, and more specifically, to a linear actuator that is used in a gas regulating valve of a breathing assistance device.

BACKGROUND OF THE INVENTION

A variety of breathing assistance devices, which we will also generally refer to as "respirators" in this text, are available today. These respirators are equipped with a source of respiratory pressurized gas. They are generally referred to as "autonomous" because an external pressurized gas feeding is not required to operate them. These devices provide the patient, at each inspiration, with a respiratory gas (typically ambient air to which a complementary gas such as oxygen can be added).

Different types of respirators are known. These different types of respirators can be classified according to their size, because the size of these devices is an important parameter. It is generally desirable to minimize the size of the respirator in order to facilitate the operation of the respirator in multiple different locations, for instance, at home as well as in the hospital. In addition, smaller sized respirators tend to increase the mobility of the patient.

Non-Transportable Respirators

A first type of respirator is generally referred to as a non-transportable respirator. A non-transportable respirator is schematically illustrated in FIGS. 1a to 1d. Such devices are generally equipped with a respiratory gas source S1 having a very large size and/or weight. This gas source can be internal to the device, or external to the device. The source of gas S1 is commonly coupled to the patient P through two ducts, however, a single duct may be used. An inspiration duct 11 is dedicated to the inspiration phase, and it carries pressurized gas from the source of gas to the patient P during inspiration. An expiration duct 12 is dedicated to the expiration phase, and it carries expiratory gases, such as carbon dioxide, which are exhaled by the patient during the expiration phase.

These non-transportable respirators are further provided with an inspiratory valve 13 and an expiratory valve 14. These two valves are located close to the gas source S1 on the inspiration duct 11 and on the expiration duct 12, respectively. The inspiratory valve 13 controls the flux of the pressurized gas transmitted to the patient during the respiratory phases. The expiratory valve 14 allows the expiratory gases of the patient to pass out of the expiratory duct 12, and into the surrounding atmosphere. The expiratory valve can be controlled based on a Positive End Expiratory Pressure (PEEP) control scheme.

Most of the operating modes of the respirators require monitoring of the expiratory gas flow and/or expiratory pressure. Therefore one or more sensors 19 for sensing the gas flow and/or pressure are located in the expiration duct 12. Each sensor usually needs to be connected to the central unit 10 of the respirator by at least three wires, in order to be supplied with power and to convey data. Therefore the sensors 19 are generally located near the gas source S1 in order to avoid further increasing the complexity of the already quite complex and large double transmission circuit by the addition of sensors and wires. Both the inspiratory and expiratory valves require specific and often complex control systems, usually in the form of a processor or controller 15, which is coupled to or otherwise in communication with the valves and the sensor 19.

Non-transportable respirators are generally provided with relatively long ducts, typically of about 150 to 180 cm. This configuration results in a high breathing resistance, which increases the work of breathing for the patient. Indeed, if the expiratory valve 14 is located at the end of the expiration duct 12 near the gas source S1 (the "distal end"), and the expiration duct 12 is relatively long, the patient P will need to "push" his expiration through the expiration duct 12 until the expired air reaches the expiration valve 14 wherein it is vented to the atmosphere.

When connected to a non-transportable respirator, the patient P will always be able to expire through the expiration duct 12, even if the gas source S1 is disabled, as shown in FIG. 1d. During expiration, the positive pressure of the expiratory gases will cause a safety backflow valve 16 on the inspiration duct 11 to close, and the expiration valve 14 on the expiration duct 12 to open. Thus, the patient will be able to expel expiration gases.

Also, if the gas source S1 is disabled, the patient will be able to draw in atmospheric gases through the inspiration duct 11. As shown in FIG. 1c, during the inspiration phase, the patient will be able to draw in atmospheric gas through the safety back flow valve 16 on the inspiration duct, and the expiration valve 14 on the expiration duct 12 will be closed. The safety back flow stop valve 16 is not located on the expiration duct 12 because it would be dangerous for the patient P to inspire through the expiratory duct 12, which usually contains expired carbon dioxide.

Transportable Respirators

A second type of respirator can be referred to as transportable respirators. A transportable respirator is schematically illustrated in FIGS. 2a to 2d. This transportable respirator is provided with a central unit 20 comprising an internal respiratory gas source S2. The gas source S2 may be a small turbine or blower, having optimized characteristics in order to limit the volume occupied by the device.

These transportable respirators typically use a single gas transmission duct 21 between the source S2 and the patient P, in contrast with devices having two ducts (an inspiration duct and an expiration duct). The respirators use an expiratory valve 22 located on the single duct 21, near the patient P (i.e. at the proximal end of the duct). In contrast to the above-described non-transportable respirators, the proximal location of the expiratory valve 22 eliminates the breathing resistance phenomenon during the expiratory phase which is caused by the length of the duct in a non-transportable respirator between the patient and the expiratory valve.

In typical transportable respirators, as illustrated in FIGS. 2a to 2d, the expiratory valve 22 is a pneumatic valve that is operated by a pressurized air feeding conduit 23, coupled between the respiratory gas source S2 (or to another source of pressure such as an independent micro-blower) and an obstructing cuff 24 of the expiratory valve 22. The pressure from the gas source S2 inflates the obstructing cuff 24 during the inspiration phase to ensure that the gas traveling along the transmission duct 21 is delivered to the patient P.

The control of the expiratory valve thus requires a second conduit 23, which obviously limits the miniaturization of the respirator, particularly the breathing circuit. During the expiration phase, the expiratory valve 24 is either opened or partially closed in order to establish a positive end expiratory pressure (PEEP) in the gas transmission duct to balance the residual overpressure in the patient lungs. In order to establish such a PEEP, it is necessary to control, very precisely, the pneumatic inflating pressure of the cuff 24 of the expiratory valve 22. This increases the complexity of the controller 25 of the respirator.

In some respiratory modes, the expiratory valve 22 has to be operated as much as possible in real time, which is quite difficult in such expiratory valves because of the pneumatic inertias which are associated with them. Moreover the configuration of such a known respirator imposes a limitation of the value of the PEEP at around 20 $cmH_2O$, while some respiratory modes would need a higher value of the PEEP (e.g. 40 $cmH_2O$ or even more).

For the same reason as for non-transportable respirators, the expiratory gas flow and/or expiratory pressure may have to be controlled, and thus gas flow and/or pressure sensors 29 will typically be provided near the expiratory valve 22. Here again, this requires providing wires along the gas transmission duct 21 between the central unit 20 and the patient P. Usually three wires (two for power supply and one for data transmission) are provided for each pressure sensor and each gas flow sensor. Since expiratory gas flow and pressure generally have to be measured, a connection cable 26 of at least five wires is thus required between the central unit 20 and the expiratory valve 22 at the proximal end of the device.

In order for the patient to safely use such a transportable respirator, the device must allow the patient to breathe in any situation, including if the pressurized gas source is disabled. With a respirator having a single gas transmission duct 21 and a separate conduit 23 for pneumatic control of the expiratory valve 22, the patient P can always expire through the pneumatic expiratory valve 22, even if the pneumatic feeding of the expiratory valve 22 is disabled, as shown in FIG. 2d. Indeed, if the pneumatic feeding of the expiratory valve is disabled, which would be the case when the gas source is disabled, the cuff 24 of the expiratory valve 22 will not be inflated, and the patient P will be able to expire expiratory gases $E_P$ through the expiratory valve 22. In such case, it will be impossible for the patient P to inspire through this pneumatic expiratory valve 22, since the cuff 24 will obstruct the passage. However, the patient P will be able to inspire via the safety back flow stop valve 27 located on the inspiration conduit 21, as shown in FIG. 2c. As shown in FIG. 2a, this safety valve 27 will normally be closed under the effect of the pressure feeding $G_s$ coming from the gas source S2. But if the gas source S2 is disabled, the pressure of the patient inspiration $I_P$ will open the safety valve 27, allowing the patient P to inspire air from outside, as illustrated in FIG. 2c.

In order to allow a safe inspiration through the safety valve 27 and the whole length of the duct 21, the diameter of the duct must be relatively large. There are generally pressure loss standard requirements to fulfill for addressing this issue of safety. For example, the French standards state that the maximum pressure loss between the source and the patient must not exceed 6 hPa for 1 liter/second for an adult and 6 hPa for 0.5 liter/second for a child. In order to fulfill these requirements, the transmission duct of typical devices as illustrated in FIGS. 2a to 2d must have a minimum diameter of 22 mm for an adult, and a minimum diameter of 15 mm for a child. The requirement for such large diameter ducts is an obstacle to miniaturization of the device, particularly the breathing circuit.

For the same reasons as for the transportable respirators, the diameters of the ducts on the non-transportable respirators illustrated in FIGS. 1a-1d must be relatively large to fulfill the pressure loss requirements. That is, the ducts must have a diameter of at least 15 mm for children and 22 mm for adults in order to allow a safe inspiration through the safety valve 16. And here again, such large duct diameters is an obstacle to miniaturization.

The pathologies and diseases to be treated by the above-described respirators are varied, and the breathing assistance devices can therefore be of different types. The respirators can be pressure-controlled or volumetric-controlled, and they can be operated according to different operating modes. Each operating mode is defined by particular setting and checking variables, but also by a particular type of material.

Some respirators, which can be referred to as hybrid respirators, are able to work according to several operating modes. However their material configuration, in particular the accessories (such as the type of ducts between the gas source and the patient, the presence of an expiratory valve, the use of a mask with apertures, etc.), must be adapted to the chosen operating mode.

It would be desirable to allow a single device to operate according to a large variety of modes, without requiring that the device be modified for each mode, such as by adapting its ducts, accessories, etc.

SUMMARY OF THE INVENTION

One aspect of the invention relates to a linear actuator for a gas regulating valve that includes a housing, a yoke mounted inside the housing, and a bobbin that is movably mounted inside the yoke and that has first and second arms that extend from a first end of the bobbin, wherein a wire coil is wrapped around the bobbin. The linear actuator also includes a flexible circuit assembly having a central portion that is attached to the yoke and first and second extensions that extend from the central portion and that are attached to the first and second arms of the bobbin, respectively. First and second electrical contacts are formed on the central portion, the first and second electrical contacts being coupled, respectively, to first and second ends of the wire coil. The linear actuator also includes a magnet that is attached to the yoke. Preferably the linear actuator, the housing, yoke, bobbin and magnet have a generally cylindrical shape.

Another aspect of the invention relates to a gas regulating valve that includes a linear actuator having a central passageway extending therethrough, a first housing portion configured to be attached to a gas delivery tube, and a second housing portion configured to be attached to a patient interface. One of the first and second housing portions extends at least partially through the central passageway of the linear actuator. The linear actuator can actuate a membrane assembly that is coupled between the first and second housing portions such that a gas passing through the first and second housing portions and through the membrane assembly is isolated from the linear actuator.

Another aspect of the invention relates to a method of manufacturing a gas regulating valve that includes the steps of inserting a first end of a first housing portion through a linear actuator to form a first section of a central passageway, inserting a membrane assembly into the first end of the first housing portion and coupling a first end of the membrane assembly to the first housing portion to form a second section of the central passageway, connecting the first housing portion and a second housing portion by a latch system on their external surface such that the second housing portion provides the third section of the central passageway and the gas regulating valve is encapsulated in one unit. The full actuating of the linear actuator couples a second end of the membrane assembly to the second housing portion such that a through central gas passageway is formed by the first housing portion, the membrane assembly and the second housing portion, and the gas passageway being isolated from the linear actuator.

Another aspect of the invention relates to a method of manufacturing a linear actuator that includes the steps of inserting a hollow bobbin having a wire coil wound thereon inside a hollow yoke, attaching a central portion of a flexible circuit assembly to the yoke, the flexible circuit assembly having first and second arc-shaped extensions protruding from the central portion, and coupling first and second ends of the wire coil to the first and second arc-shaped extensions of the flexible circuit assembly. The method also includes the steps of inserting a hollow magnet inside the cylindrical bobbin, and attaching the magnet to the yoke.

Another aspect of the invention relates to a method of treating a patient with a breathing assistance device which includes a gas supply, a patient interface, a gas supply line coupling the gas supply and the patient interface, and a gas regulating valve that controls a flow of the gas from the gas supply to the patient interface, wherein the gas regulating valve includes a linear actuator that is sealed off from the patient airway. The method includes the steps of sensing a gas pressure in one of the supply line and the patient interface, and sending a control signal which is based on the sensed gas pressure to the linear actuator of the gas regulating valve to cause linear movement of a coil of the linear actuator, wherein the linear movement of the coil causes an obstruction member of the gas regulating valve to move.

Another aspect of the invention involves a method of treating a patient with a breathing assistance device which includes a patient interface with a linear actuator that controls a size of an exhalation vent of the patient interface, wherein the linear actuator is sealed off from the patient airway, a gas supply and a supply line coupling the gas supply and the patient interface. The method includes sensing a gas pressure in at least one of the gas supply line and the patient interface, and sending a control signal which is based on the sensed gas pressure to the linear actuator to cause linear movement of a coil of the linear actuator, wherein the linear movement of the coil causes an obstruction member of the exhalation vent to move.

Another aspect of the invention involves a breathing assistance device that includes a gas supply, a patient interface, a gas supply line coupling the gas supply and the patient interface, and a gas regulating valve coupled between the gas supply and the gas supply line. The gas regulating valve controls a flow of the gas from the gas supply to the patient interface, and the gas regulating valve includes a linear actuator that is sealed off from the patient airway.

Another aspect of the invention involves a breathing assistance device that includes a gas supply, a gas supply line coupled to the gas supply, a patient interface, a pressure sensor that senses a pressure within the patient interface, and a gas regulating valve coupled between the gas supply line and the patient interface. The gas regulating valve includes a movable obstruction member that moves between a closed position at which the gas regulating valve couples the gas supply line to the patient interface and an open position at which the gas regulating valve couples the patient interface to the atmosphere. the breathing assistance device also includes a controller that is coupled to the pressure sensor and the gas regulating valve. The controller sends a control signal to the gas regulating valve that controls a degree to which the obstruction member moves from the open position toward the closed position. The controller calculates an expiratory flow of the patient when the patient is exhaling based upon a pressure within the patient interface, as sensed by the pressure sensor, and a value of the control signal sent to the gas regulating valve.

Another aspect of the invention involves a method of calculating a patient's expiratory flow when the patient is using a breathing assistance device that includes a patient interface that is coupled to a gas regulating valve, and wherein a control signal is applied to the gas regulating valve to control a flow through gas regulating valve. The method includes determining a pressure difference between a pressure within the patient interface and atmospheric pressure while the patient is expiring, determining a value of the control signal applied to the gas regulating valve while the patient is expiring, and calculating the patient's expiratory flow based on the determined pressure difference and the determined value of the control signal.

Further aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 1a-1d illustrate a background art non-transportable respirator;

FIGS. 2a-2d illustrate a background art transportable respirator;

FIG. 3 is a schematic representation of a breathing assistance device;

FIGS. 4a-4c illustrate operating modes of gas regulating valve;

DETAILED DESCRIPTION OF PREFERRED EMBODIMENTS

Figure 1B:
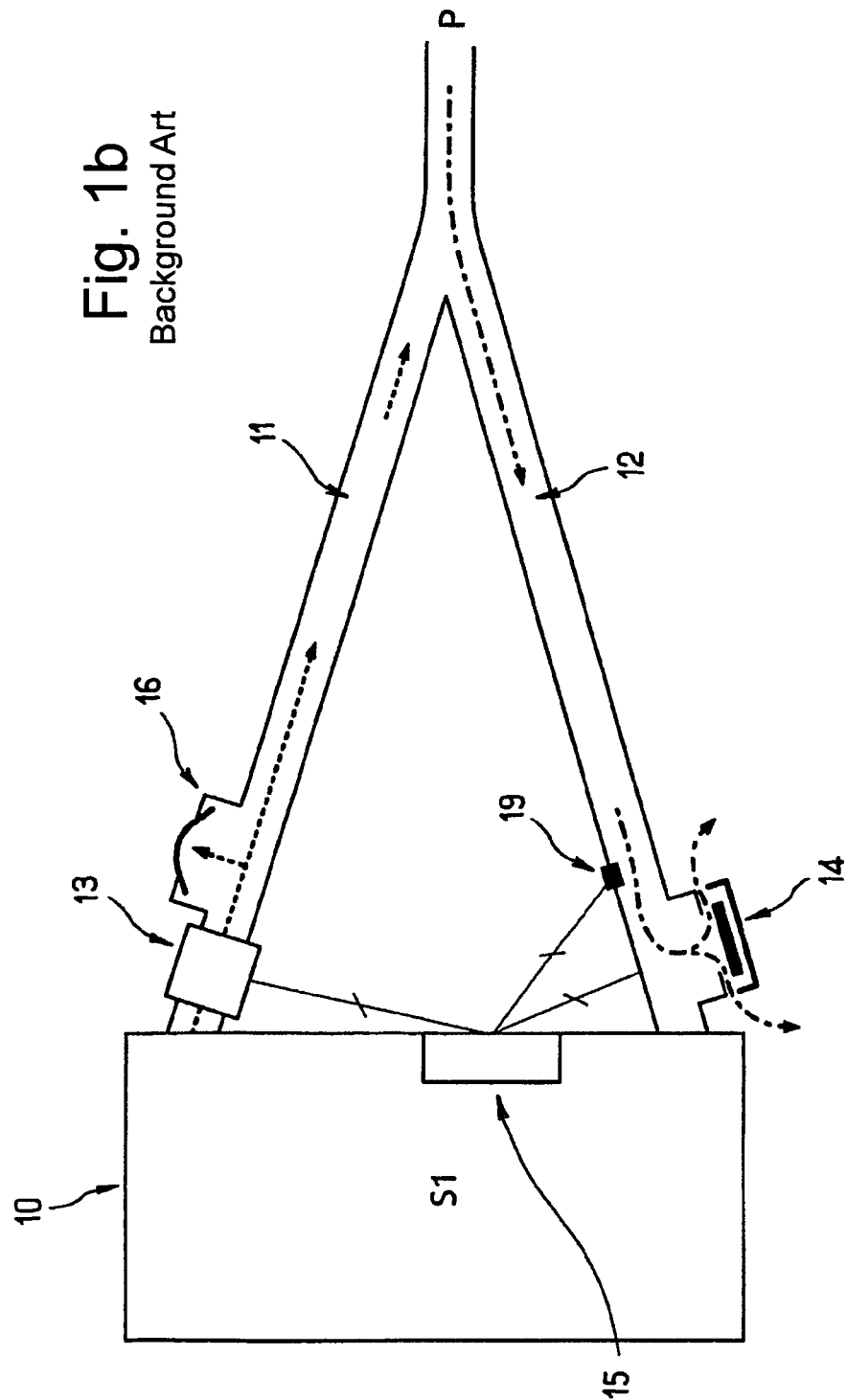
Figure 2C:
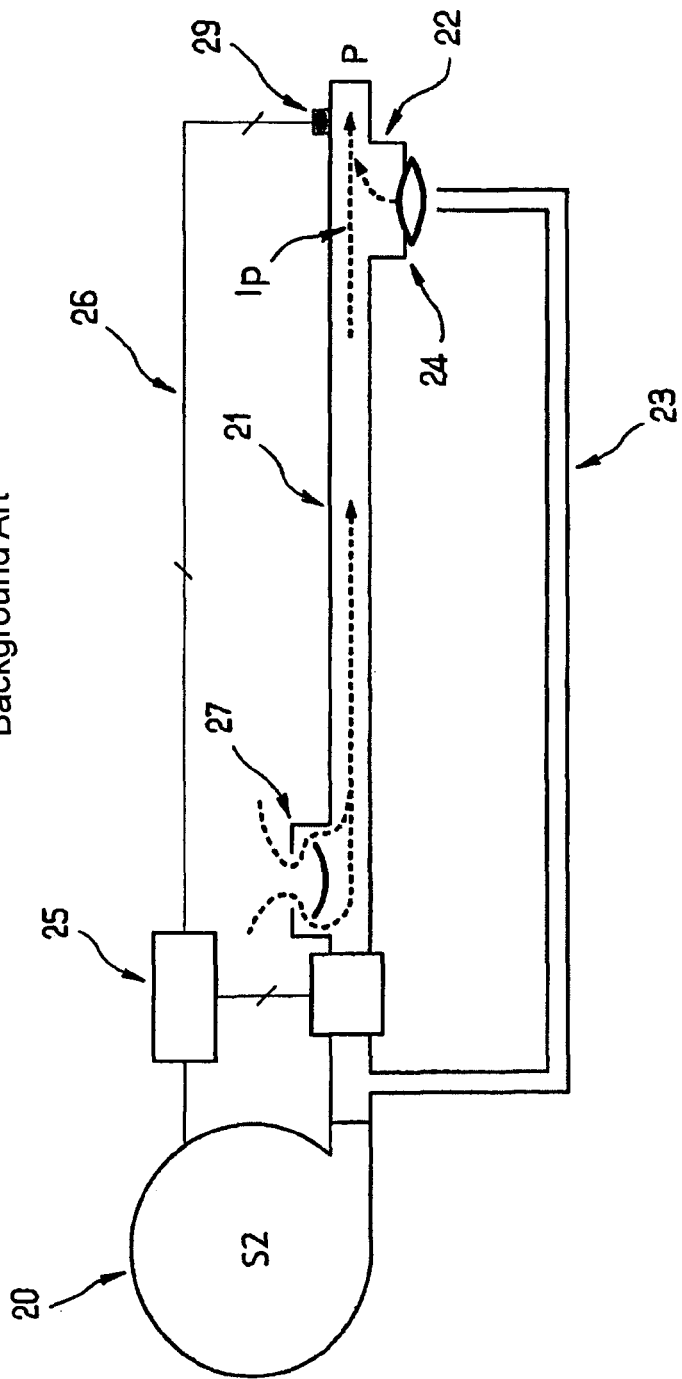

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including," and thus not limited to its "closed" sense, that is the sense of "consisting only of." A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

General Structure of Respirator and Breathing Assistance Device

We shall first describe the general structure of a device which can be used as a respirator, or a breathing assistance device, as illustrated in FIG. 3. Some embodiments of the device could also be used as a continuous positive airway pressure (C-PAP) device for treating sleep apnea and other similar conditions. For instance, the device could be part of a ventilator operating in a C-PAP mode.

Also, because the gas regulating valve is highly controllable, the device can also be used as a Bi-level positive airway pressure (Bi-PAP) device which delivers air or gas at a higher pressure during inhalation than during exhalation. The device could also be operated in a mode where the gas pressure is under active variable control.

This device comprises a central unit 30, which itself includes an internal gas source S for supplying a patient P with respiratory pressurized gas. The gas source S is typically a small blower. In some instances, the gas source could also include an oxygen blender capable of introducing selected amounts of oxygen into the gas being delivered to the patient. Details of an oxygen blender system can be seen in International Application No. PCT/IB2005/002326 (Publication No. WO 2006/136878), which was filed on Jun. 23, 2005, the contents of which are hereby incorporated by reference. The breathing assistance device further comprises a gas transmission circuit between the central unit 30 and the patient P, so as to allow the patient P to inspire and expire.

A gas regulating valve 32 is interposed in said gas transmission circuit at a proximal location. The term "proximal location" means that the gas regulating valve 32 is located near (e.g., typically a few centimeters) the end of the gas transmission circuit coupled to the patient P. As shall be described further in this text, the regulating valve can be made according to many different embodiments, some examples of which are described below. Additional embodiments of such a gas regulating valve can be seen in International Application No. PCT/EP2006/061989 (Publication No. WO 2006/117379), filed on May 2, 2006, the contents of which are hereby incorporated by reference.

The gas source S will preferably be capable of operating according to several respiratory modes. This gas source is connected to an air inlet 33*a* for collecting ambient air to be provided to the patient P. An additional inlet 33*b* may also be provided for a secondary respiratory gas such as oxygen, in order to enrich the ambient air. The gas source S is powered through a power supply 37. This power supply 37 may be an internal battery or an external power supply.

The gas transmission circuit may be composed of one or more gas transmission ducts. As shown in FIG. 3, in one embodiment, the breathing assistance device includes a gas transmission circuit consisting of a single gas transmission duct 31. This gas transmission duct 31 comprises a distal end 31*d* coupled to the source S and a proximal end 31*p* coupled to the patient P. The proximal end 31*p* of the transmission duct 31 is connected to the patient P through a connecting device, e.g., a patient interface 36. This patient interface 36 may be a device adapted for tracheotomy or a mask, such as a nasal mask, a full face mask, or the patient interface could be adapted to connect to nasal inserts, nasal plugs and other such devices. In an alternate embodiment, the breathing assistance device may include two separate gas transmission ducts, one for inspiration and one for exhalation.

The breathing assistance device further includes a processor or controller 35 for controlling the gas regulating valve 32 via a connection link 39, which is used for data transmission and power supply. This connection link 39 can be a connection cable 39. The controller 35 is coupled to one or more measurement devices, i.e. sensors 34. The sensors would typically include a gas flow sensor and a pressure sensor, which are coupled to the controller 35 via the connection cable 39. Part or all of these sensors can be located proximally, that is located near the gas regulating valve 32. It is also possible that part or all of these sensors are located on another part of the gas transmission duct 31, such as near its distal end 31*d*. The controller 35 further includes a data processing device for processing of the signals coming from the different sensors, which could include hardware, software and possibly firmware.

In some embodiments, the data processors of the controller 35 can be located at a distal position, that is on the gas source S. In other embodiments, the data processors may be located at a proximal position, that is near the patient P. Indeed, the more sensors there will be near the gas regulating valve 32, the more wires there will have to be in the connection cable 39 along the gas transmission duct 31. To help reduce the number of wires, it may be advantageous to provide a proximal data processor 38 adjacent the gas regulating valve 32 so that multiple different signals from the sensors can be processed at the proximal location, and then transmitted to distal data processor of the controller 35 through a single data transmission wire. In this instance, it may only be necessary to have three wires, i.e. one data transmission wire and two power supply wires.

The gas transmission duct 31 may be of different diameters. In particular, this gas transmission duct 31 may have a smaller diameter than the ducts used in the known breathing assistance devices such as those represented in FIGS. 1a-1d and 2a-2d. As will be explained in more detail below, the characteristics of the gas regulating valve 32, which is interposed in the gas transmission duct 31, allows this type of breathing assistance device to fulfill the pressure loss and safety standards without needing a relatively large diameter duct. It is therefore possible for the gas transmission duct 31 to have an external diameter smaller than 22 mm for adults (19 mm internal diameter) and smaller than 15 mm for children. For example the gas transmission duct for adults may have an internal diameter of between 10 mm and 18 mm, or between 12 mm and 17 mm, such as 15 mm.

The gas regulating valve 32 is controlled in a manner independent of the pneumatic pressure supplied to the valve, so that no separate air feeding conduit is required to operate the valve. For example the gas regulating valve 32 may be electrically controlled. This also allows the gas regulating valve to respond faster in real time as there is no pneumatic inertia to delay the response. This leads thus to a more compact device. Miniaturization of the breathing assistance device is further increased when using data processors 38 located on the gas regulating valve, i.e. proximally. Despite these differences from the related art breathing assistance devices described above, the breathing assistance device remains also highly safe and reliable.

Operational Methods of the Gas Regulating Valve

The gas valve described above is configured so that even if there is a breakdown of the gas source or the controller, the patient will be able to breathe. This will be explained with references to FIGS. 4a-c, 5a and 5b, which together illustrate the basic operational concepts of the above-described valve.

Figure 5A:
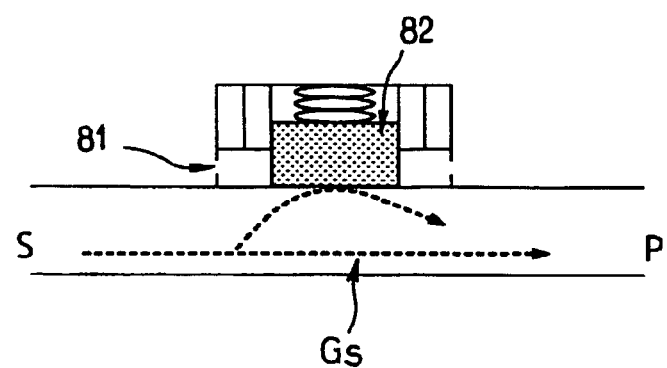
FIGS. 5a and 5b illustrate operating modes of another type of gas regulating valve.
Figure 5B:
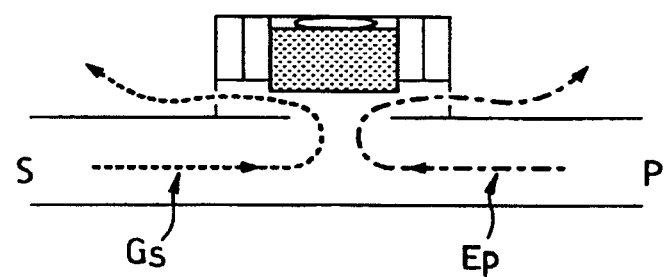

FIGS. 4a-c illustrate a first type of valve where a cylindrical obstruction element either blocks or opens apertures on an exterior of the cylindrical valve body. In this embodiment, the gas traveling from the gas source to the patient would travel down the center of the cylindrical obstruction element. FIGS. 5a and 5b illustrate a different valve construction where the blocking element is located off to one side of the gas main passageway. Although the valve is illustrated as a cylinder having a circular cross-sectional shape, it is noted that the valve may have other cross-sectional shapes such as square, rectangular, or any other geometric shape.

The normal operation of the device corresponds to the case when both the gas source S and the controller 35 are operating normally. As shown in FIGS. 4a and 5a, during the inspiration phase, the obstruction element 72/82 is positioned so that an aperture 71/81 is obstructed. As a result, pressurized gas Gs coming from the gas source S is transmitted to the patient P.

As shown in FIGS. 4b and 5b, during the expiration phase, the aperture 71/81 is at least partially open, which allows gas to circulate between an inside and an outside of the valve. As a result, when the patient exhales, the open aperture allows expired gas to exit the valve through the aperture 71/81. By controlling a size of the opening, one can control the positive exhalation pressure in a PEEP mode. In some instances, it is important to carefully control the PEEP in the gas transmission so that the patient can expire correctly. Controlling the PEEP is a way to balance the residual overpressure in the patient's lungs. To exert control of the PEEP, the position of the obstruction element 72/82 is controlled in real time based on a sensed pressure in the gas transmission duct.

If the gas source S becomes inoperative, the patient must still be allowed to breathe. In this circumstance, the controller of the breathing assistance device will cause the obstruction element to assume a position which leaves the aperture 71/81 at least partially open during both inspiration and exhalation. During the inspiration phase, because the aperture is open, the patient will be able to inhale air from the surrounding atmosphere via the aperture. During the expiration phase, the controller may still carefully control the position of the obstruction element, to thereby maintain the correct PEEP.

When the controller itself is disabled, the obstruction element cannot be controlled. Therefore, a return mechanism is provided to ensure that the aperture remains open whenever the controller is not functional. This allows the patient to inhale from and exhale to the atmosphere through the aperture. However, because the position of the obstruction element cannot be controlled, it is not possible to control the PEEP.

In the embodiment illustrated in FIGS. 4a-c, a magnet 73 and coil 74 are used to control the position of the obstruction element 72. These elements are designed so that when no signals are supplied to the coil 74 from a controller, the magnetic attraction between the coil and the magnet ensure that the obstruction element 72 assumes the open position, as shown in FIG. 4c. Of course, in alternate embodiments, a return device, such as a biasing spring element, could also be used to ensure that the obstruction element 72 returns to a position that leaves the aperture 71 open.

In the embodiment illustrated in FIGS. 5a and 5b, a magnet and coil also control a position of the obstruction element. However, a return spring is also provided to bias the obstruction element 82 to the open position. Thus, when no signals from the controller are sent to the coil, the obstruction element 82 assumes the open position, as shown in FIG. 5b.

Linear Actuator

Figure 6A:
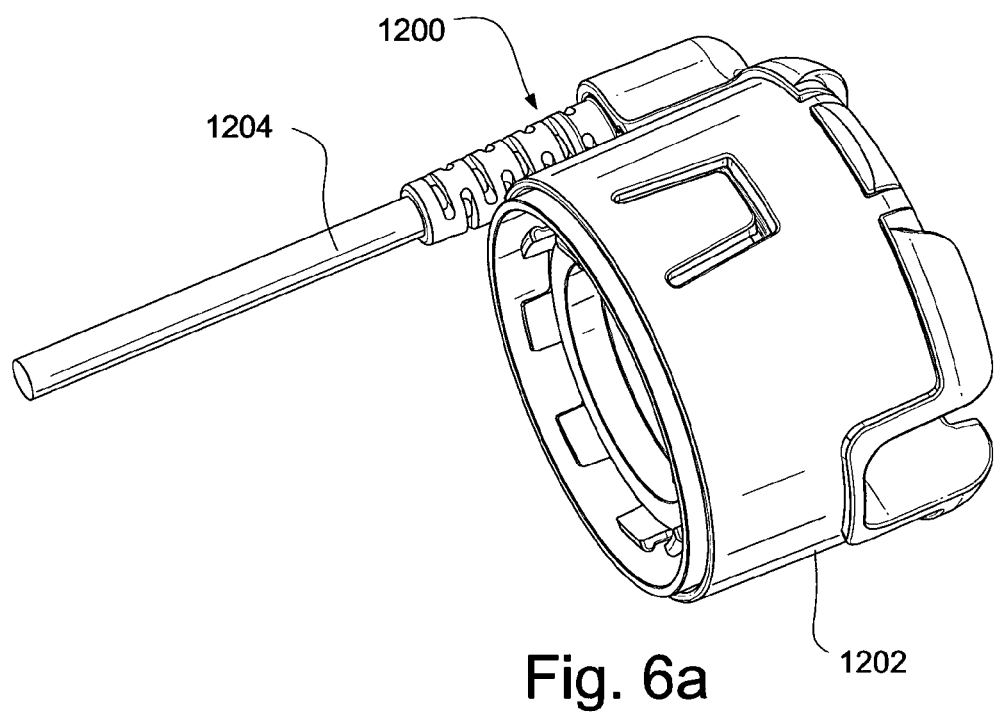
FIGS. 6a and 6b are perspective views of a linear actuator that can be used in the gas regulating valves described above.
Figure 6B:
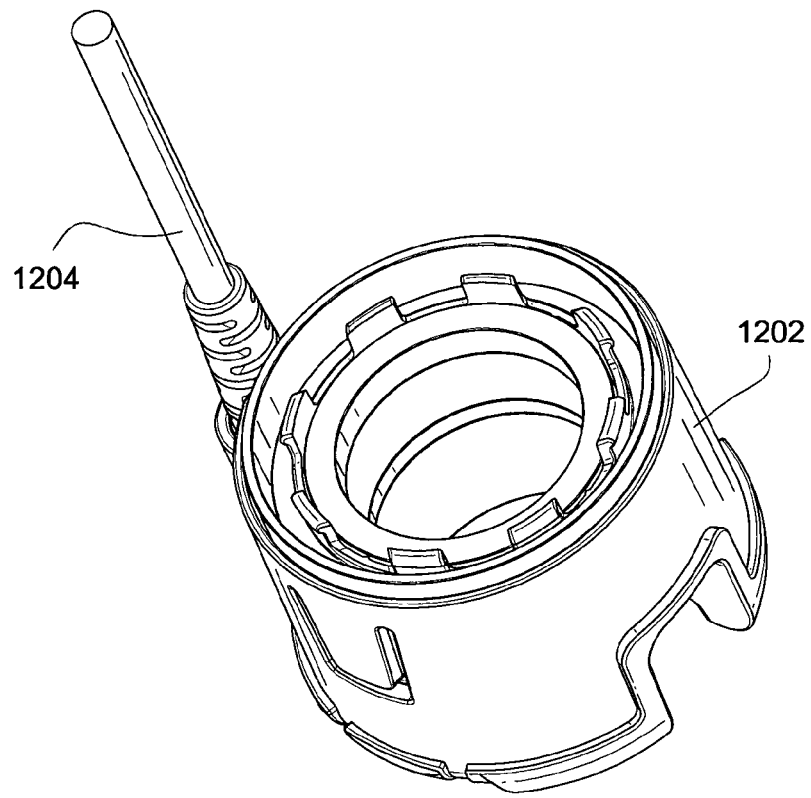

FIGS. 6a and 6b illustrate a linear actuator which could be used in a gas regulating valve as described below. The linear actuator 1200 includes a housing 1202 which houses a movable coil assembly and a magnetic element. A cable assembly 1204 provides electrical connections to the coil of the linear actuator 1200. The linear actuator has a central aperture adapted to form a passage for receiving a gas flow path. The moveable coil assembly and magnetic element are provided around the periphery of the actuator, preferably around an annular periphery of the actuator. The linear actuator has a preferably circular shape, although other shapes may be used. The actuator moves in a linear manner.

Figure 7:
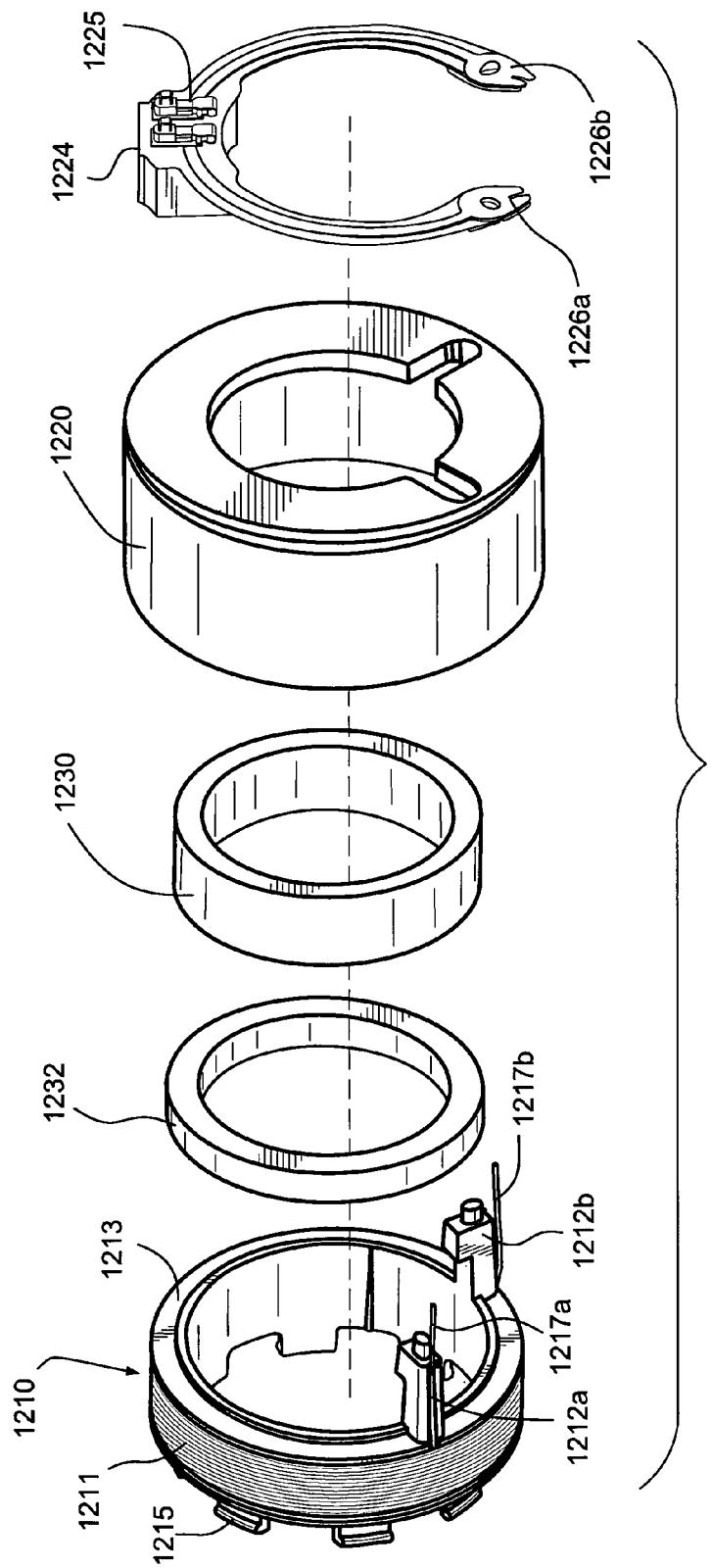
FIG. 7 is an exploded view of portions of the linear actuator shown in FIGS. 6a and 6b.

FIG. 7 illustrates the coil and magnetic elements of the linear actuator. As shown in FIG. 7, a coil assembly 1210 includes a wire coil 1211 which is wound about a bobbin 1213. The bobbin 1213 includes first and second arms 1212a, 1212b which extend upward from one side of the bobbin 1213. Free ends 1217a, 1217b of the wire coil 1211 extend up the first and second arms. Thus the arms 1212a, 1212b are wire aligning structures and the person skilled in the art would understand that other forms of such structures may be utilized. In addition, the bobbin includes a plurality of depending legs 1215 which extend downward from a second side of the bobbin which is opposite the first and second arms. These legs 1215 are projections that facilitate the movement of an obstruction member, such as a membrane, in coordination with the movement of the coil as described in more detail below. It is acknowledged that other forms of projections on the second side of the bobbin may be utilized having different shapes and sizes that facilitate the coordinated movement of the obstruction element with the movement of the coil.

In an example embodiment, the bobbin 1213 is formed of a molded synthetic material, and the wire coil 1211 is formed of coated copper wire. Of course, in alternate embodiments, other materials could be used.

The linear actuator also includes a magnet 1230, and a pole piece 1232. The magnet 1230 and pole piece 1232 preferably have a generally cylindrical shape as shown, but may have other shapes depending upon the shape of the other components of the linear actuator. The bobbin 1213 and wire coil 1211, the magnet 1230 and the pole piece 1232 all fit inside a yoke 1220. This assembly also includes a flexible circuit assembly 1224.

In an example embodiment, the magnet is a sintered NdFeB magnet which is coated with a corrosion resistant material, such as an epoxy, nickel or gold. The yoke 1220 and the pole piece 1232 are made of stainless steel. In alternate embodiments, other materials could be used for these pieces.

Figure 8:
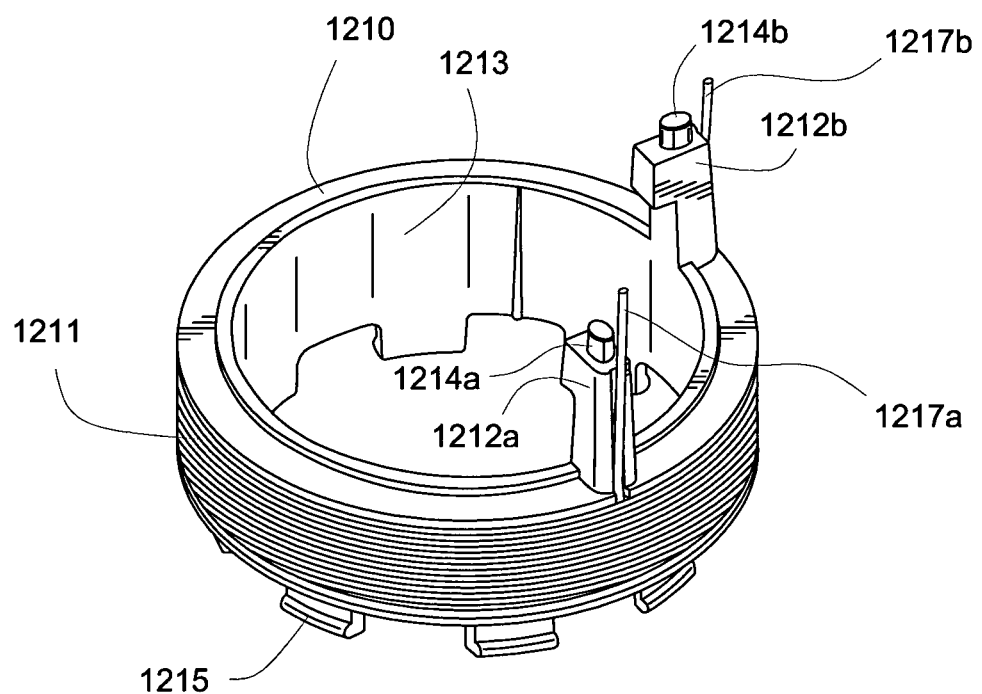
FIG. 8 is a perspective view of the coil assembly of the linear actuator.

FIG. 8 illustrates the coil assembly 1210 in greater detail. As shown therein, the wire coil 1211 is wound around the bobbin 1213. Protrusions 1214a, 1214b are formed on the ends of the first and second arms 1212a, 1212b. In some embodiments, the protrusions 1214a and 1214b are elliptical in cross-section.

Figure 9B:
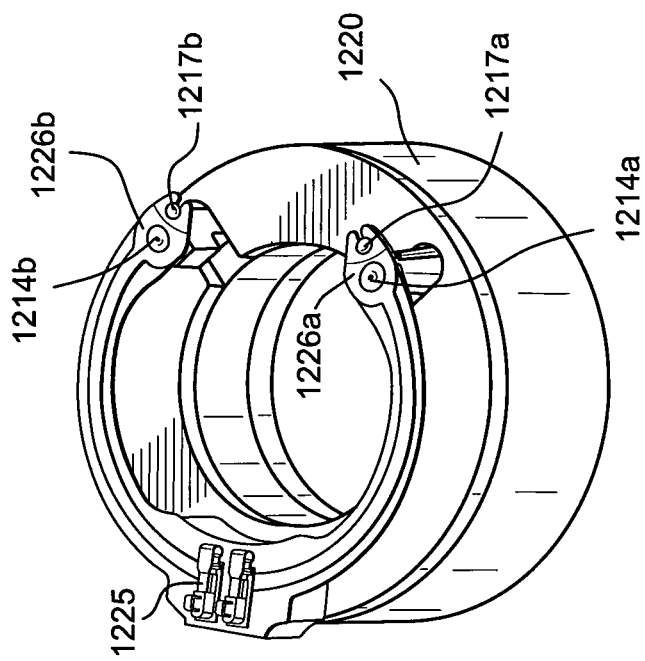
FIGS. 9a-9e illustrate steps of assembling the linear actuator shown in FIGS. 6a and 6b.
Figure 9A:
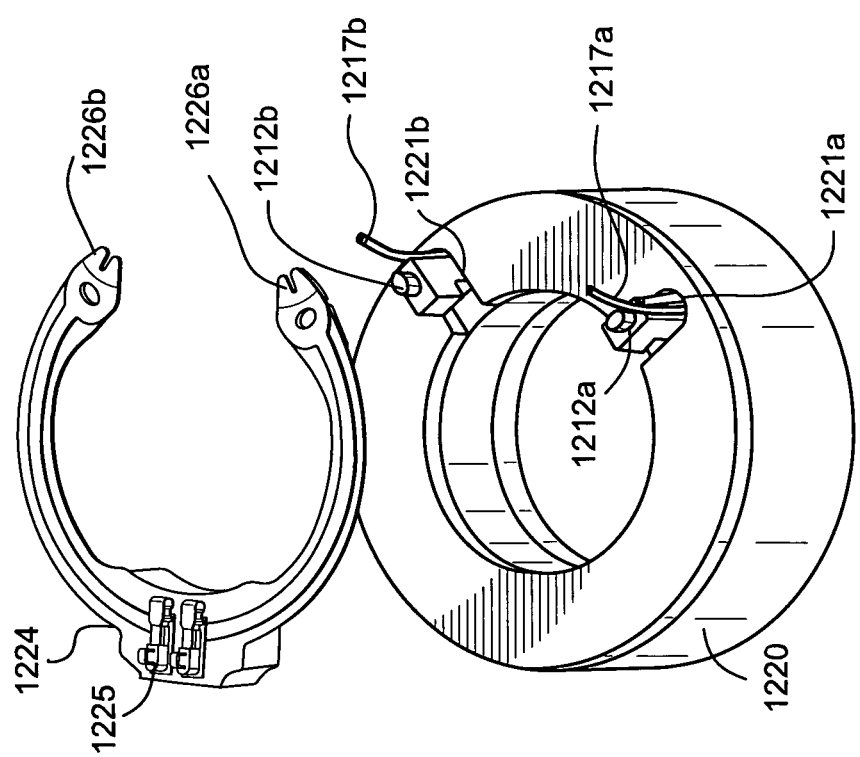

The process of assembling the linear actuator is illustrated in FIGS. 9a-9e. As shown in FIGS. 9a and 9b, the coil assembly 1210 is first inserted into the yoke 1220. There are first and second apertures 1221a, 1221b in the yoke 1220 which allow the first and second arms 1212a, 1212b of the coil assembly to protrude through the apertures. As explained above, free ends 1217a, 1217b of the coil wire 1211 would also extend up the first and second arms 1212a, 1212b and thus through the apertures 1221a, 1221b.

The flexible circuit assembly 1224 is then attached to the first and second arms of the coil assembly. The protrusions 1214a, 1214b on the top of the first and second arms 1212a, 1212b are inserted into corresponding apertures in the ends 1226a, 1226b of the flexible circuit 1224. The protrusions 1214a, 1214b on the tops of the first and second arms 1212a, 1212b could be provided or otherwise attached to the apertures in the ends of the flexible circuit 1224 via heat staking (by melting the protrusions after they have been inserted into the apertures in the flexible circuit), by an interference fit, via an adhesive, or by other suitable means.

In addition, the free ends of the wire coil 1217a, 1217b would be inserted into notches formed in the ends 1226a, 1226b of the flexible assembly 1224. The ends 1217a, 1217b of the wire coil 1211 can be attached to the notches in the ends 1226a, 1226b of the flexible circuit 1224 by soldering, with an adhesive, or other suitable means. Any remaining free ends of the wires would then be trimmed off.

The portion of the flexible circuit 1224 underneath the electrical contacts 1225 could be attached to the top of the yoke 1220 via an adhesive or any other type of fixation method. In some embodiments, an additional mounting element may be positioned between the top surface of the yoke 1220 and the bottom surface of the flexible circuit assembly 1224 during the assembly process. In a presently preferred embodiment, a spacer element is pre-attached to the underside of the flexible circuit assembly during its manufacture to thereby simplify the final assembly of the linear actuator. The electrical contact assembly 1225 of the flexible circuit would include first and second electrical contacts which are electrically coupled to the free ends of the wire coil via conductive paths in the flexible circuit 1224.

Figure 9C:
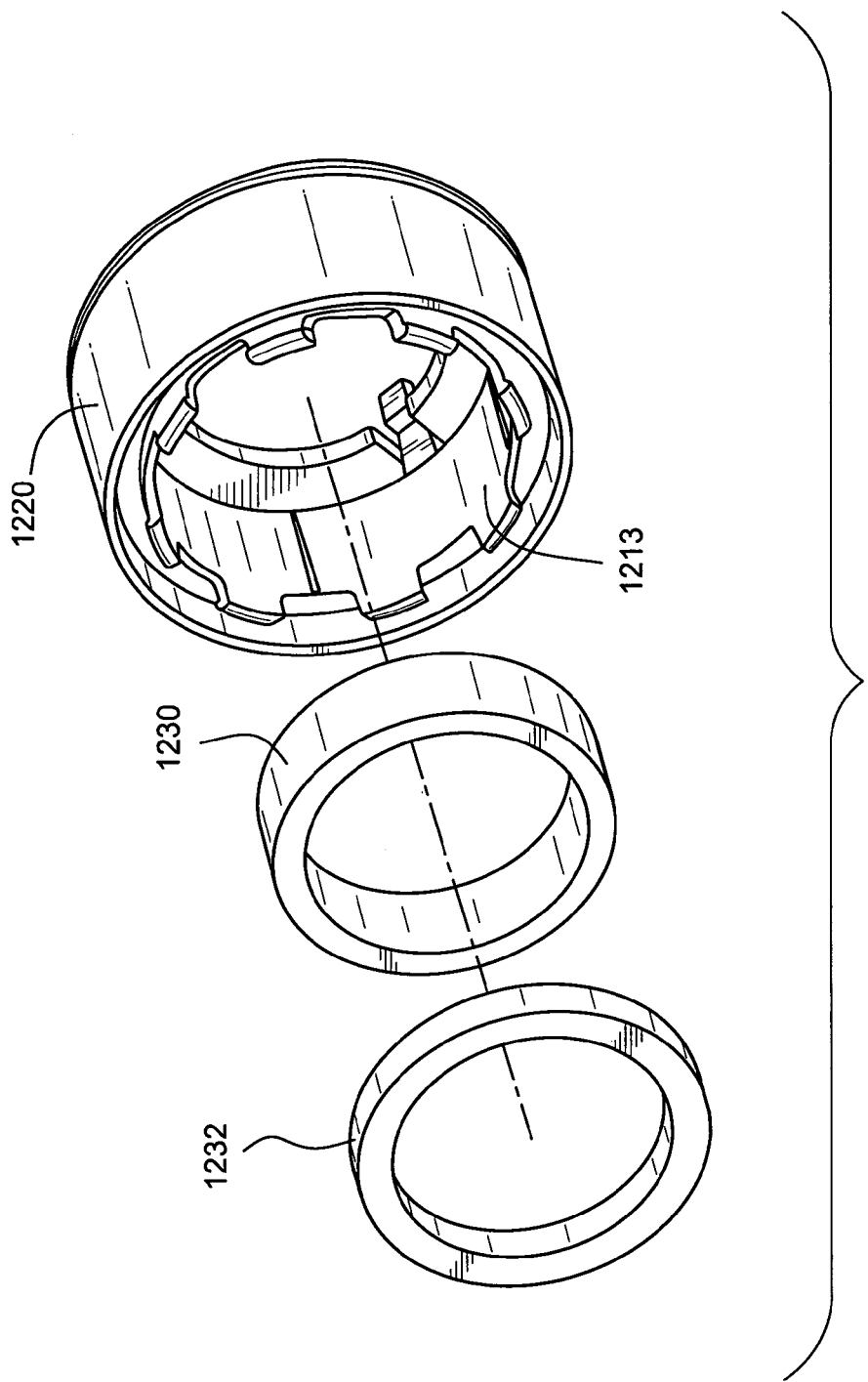
Figure 9D:
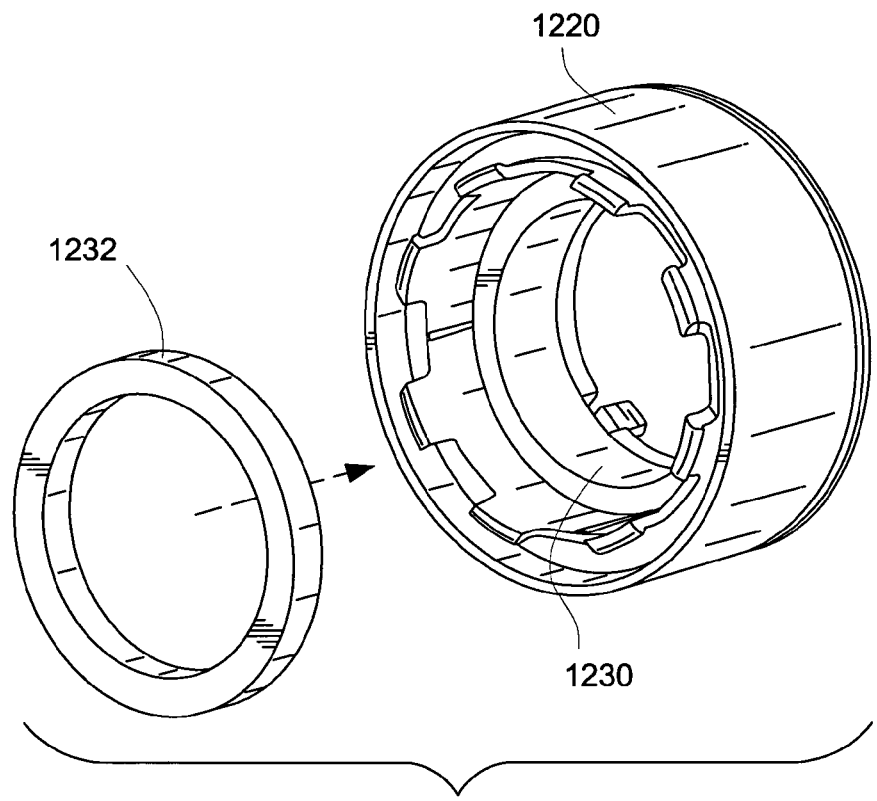
Figure 9E:
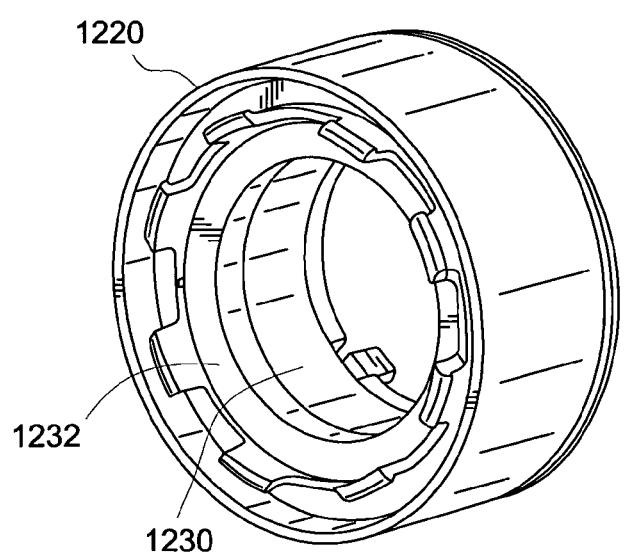

As shown in FIGS. 9c-9e, the magnet 1230 would then be mounted inside the coil assembly 1210. Next, a pole piece 1232 would be mounted inside the coil assembly 1210 and adjacent to the magnet 1230. The magnet and the pole piece could be bonded together with an adhesive to form the magnetic element. In addition, the magnet could be bonded to the yoke 1220 via an adhesive. In a presently preferred embodiment, once the magnet 1230 and pole piece 1232 have been mounted inside the coil assembly and the yoke, a wicking adhesive such as cyanoacryolate is used to bond the yoke 1220 to the magnet 1230 and the pole piece 1232.

Figure 10:
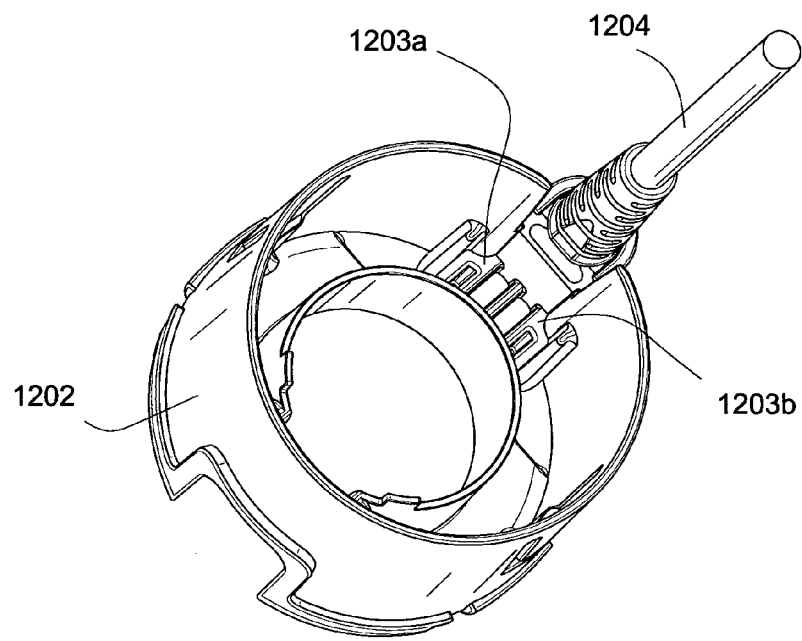
FIG. 10 is a perspective view of the housing of the linear actuator of FIGS. 6a and 6b.

As shown in FIG. 10, the cable assembly 1204 would then be inserted into a protrusion 1201 of the housing 1202. As shown in FIG. 10, first and second electrical contacts 1203a, 1203b on the cable assembly 1204, face upward within the housing 1202 after the cable assembly 1204 has been mounted inside the protrusion 1201 on the housing 1202. The two electrical contacts 1203a, 1203b would be connected to two electrical wires running through the cable assembly 1204.

Figure 11:
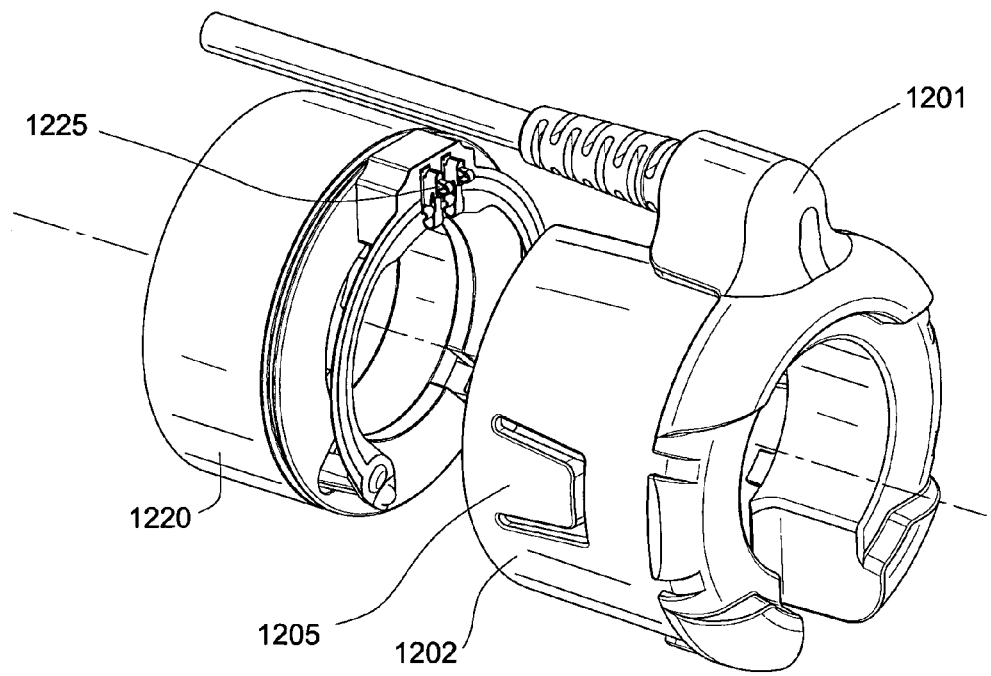
FIG. 11 illustrates the final step in assembling the linear actuator shown in FIGS. 6a and 6b.

The assembly shown in FIG. 9e, which includes the coil assembly mounted in the yoke and the magnet and pole piece mounted inside the coil assembly, would then be mounted inside the linear actuator housing 1202, as shown in FIG. 11. The electrical contacts 1225 on the flexible circuit 1224 would be aligned with the electrical contacts 1203a, 1203b on the cable assembly 1204. As a result, as the yoke 1220 is inserted into the housing 1202, the electrical contacts 1225 of the flexible circuit 1224 would engage the electrical contacts 1203a, 1203b of the cable assembly 1204. Tabs 1205 on the housing 1204 would retain the yoke, coil and magnet assembly within the housing 1202. Other means for retaining the yoke, coil and magnet assembly within the housing 1202 may be used such as latches, hooks, clamps etc. The end result is the linear actuator 1200 shown in FIGS. 6a and 6b. The structured design of the linear actuator provides easy integration and assembly of the linear actuator resulting in reduced manufacturing costs.

In the assembled linear actuator, the yoke 1220 will be fixed to the housing 1202, and the magnet 1230 and the pole piece 1232 would be fixed to the yoke 1220. Thus, these elements are intended to remain stationary. The coil assembly, which includes the wire coil 1211 wound around the bobbin 1210 would be free to move axially within the device. The depending legs 1215 of the bobbin could bear against or be attached to a movable portion of a gas regulating valve, such as an obstruction member, to control a flow of a gas through the gas regulating valve. The coil has a low mass and very low drag resulting in the linear actuator having a fast dynamic response. Having a fast dynamic response allows the linear actuator to be used in delivering a range of different ventilation modes as described in more detail below.

In an alternative embodiment the magnetic element may be movable and the coil assembly may be fixed to the yoke (i.e. remain stationary). This may provide advantages in terms of power supply wiring. However, the magnetic element has a larger weight than the coil assembly which would consequently result in a higher inertia and slower response time, thus reducing the overall efficiency of the actuator. Also a higher current demand would be required to drive movement of the magnet.

When the coil assembly of the linear actuator moves in the axial direction, the first and second arms 1212a, 1212b of the bobbin would move in the apertures 1221a, 1221b formed on the top surface of the yoke 1220. This will cause the ends of the arms 1226a, 1226b of the flexible circuit assembly 1224 to move with the arms 1212a, 1212b of the bobbin. The central portion of the flexible circuit assembly 1224 is fixed to the top surface of the yoke 1220. Thus, as the coil assembly moves in the axial direction, it will cause the flexible circuit assembly to flex.

The linear actuator is highly efficient resulting in a low power consumption while being capable of delivering the optimum force required due to the magnetic design of the actuator. Furthermore, the linear actuator has a low overall weight and size due to the highly compact design of the linear actuator. The weight of the linear actuator may be approximately 25 g to 30 g, preferably 27.5 g. The linear actuator yoke may have an external diameter of approximately 25 mm to 40 mm, preferably 30 mm and a height of the linear actuator in the fully retracted position is approximately 16 mm to 20 mm, preferably 18.7 mm. Although it is acknowledged that other sizes, shapes and weights for the linear actuator may be used whilst still being within the scope of the invention.

When the linear actuator is installed in a gas regulating valve as described above, there must be some mechanism to ensure that if power is lost, the gas regulating valve will remain in an "open" position/configuration so that a patient can still breathe. In some embodiments, a spring or other biasing element in the gas regulating valve will act to bias the obstructing element of the gas regulating valve to the open position. In some embodiments, if there is no electricity, the elasticity of the membrane itself can provide for a return spring force to open the valve, thus allowing the patient to breathe. The membrane acts as both the obstructing element and as a return spring, eliminating the need for a separate return spring.

Gas Regulating Valve with Linear Actuator

An embodiment of a gas regulating valve which makes use of a linear actuator as described will now be explained. This gas regulating valve could be used in a breathing assistance device as illustrated in FIG. 3. The design of the gas regulating valve ensures that no portions of the linear actuator are in the air path used by a patient, or are otherwise exposed to the air passing through the patient airway. As a result, it would be possible to reuse the linear actuator for multiple patients without sterilizing the linear actuator between uses.

Figure 12:
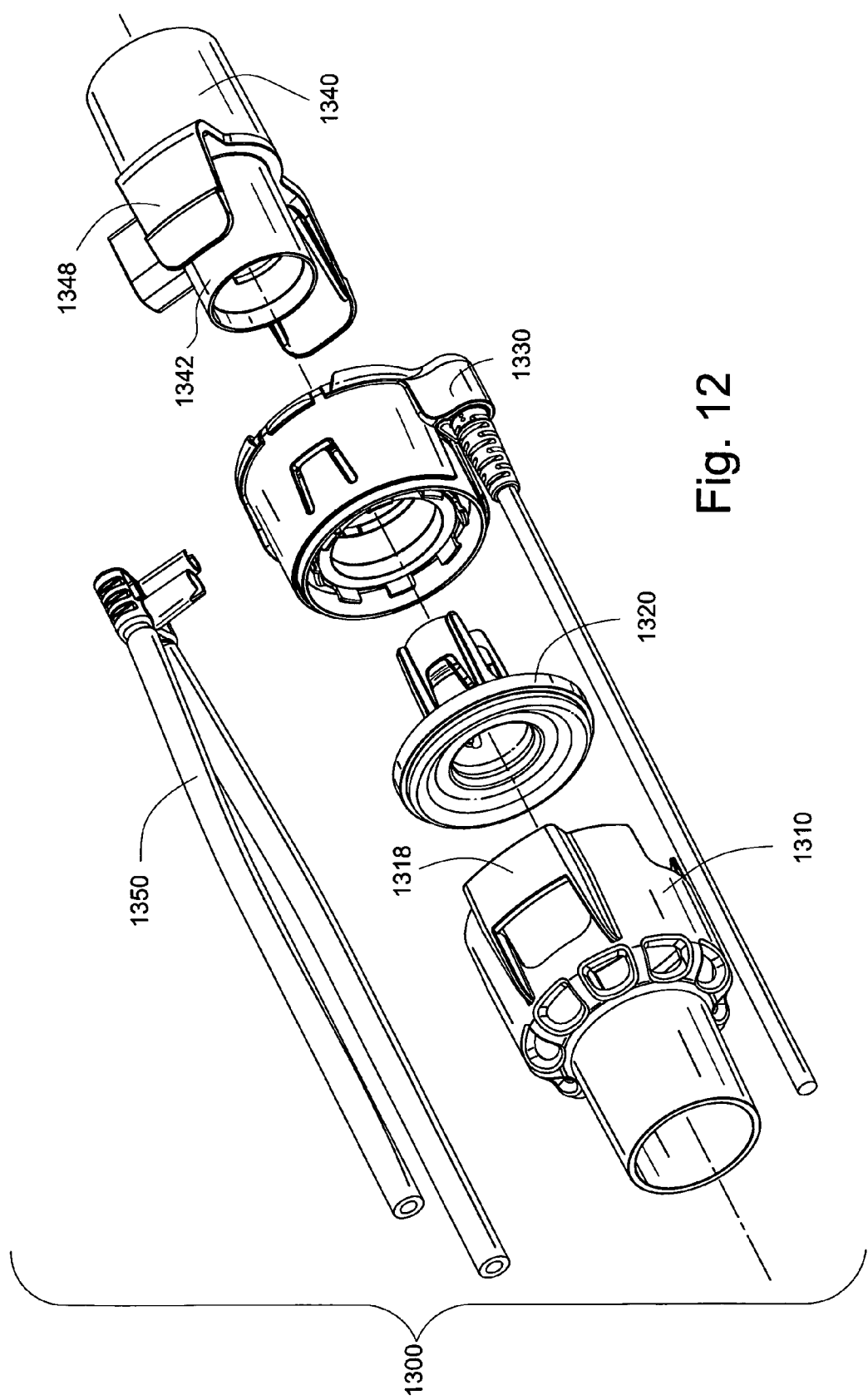
FIG. 12 is an exploded perspective view of a valve assembly that incorporates a linear actuator.

FIG. 12 illustrates the major elements of the gas regulating valve 1300. As shown therein, the gas regulating valve 1300 includes a distal housing 1310, a membrane assembly 1320, a linear actuator 1330, a proximal housing 1340 and tubes 1350 that can be used to detect the flow rate and pressure within the gas regulating valve 1300.

In the embodiment illustrated in FIG. 12, the tubes 1350 would pass from the proximal location adjacent a patient to a distal location on gas supply assembly. Sensors for sensing the pressure and flow conditions may be located at the distal location on the gas supply assembly. In alternate embodiments, gas pressure and flow sensors could be mounted on the gas regulating valve itself. A processor or controller coupled to the sensors could be located on the gas regulating valve itself at the proximal location, or at a distal location, such as on the gas supply assembly.

To assemble the gas regulating valve 1300, the protruding portion 1342 of the proximal housing 1340 would be inserted through a first end of the linear actuator 1330. The membrane assembly 1320 would be inserted into a second end of the linear actuator 1330 and connected to the protruding portion 1342 of the proximal housing 1340. The proximal housing 1340 is locked on the membrane assembly 1320, as explained in greater detail below. The distal housing 1310 is fitted over the exterior of the linear actuator module 1330. The sensing tubes 1350 are attached to corresponding apertures on the proximal housing 1340.

Figure 14:
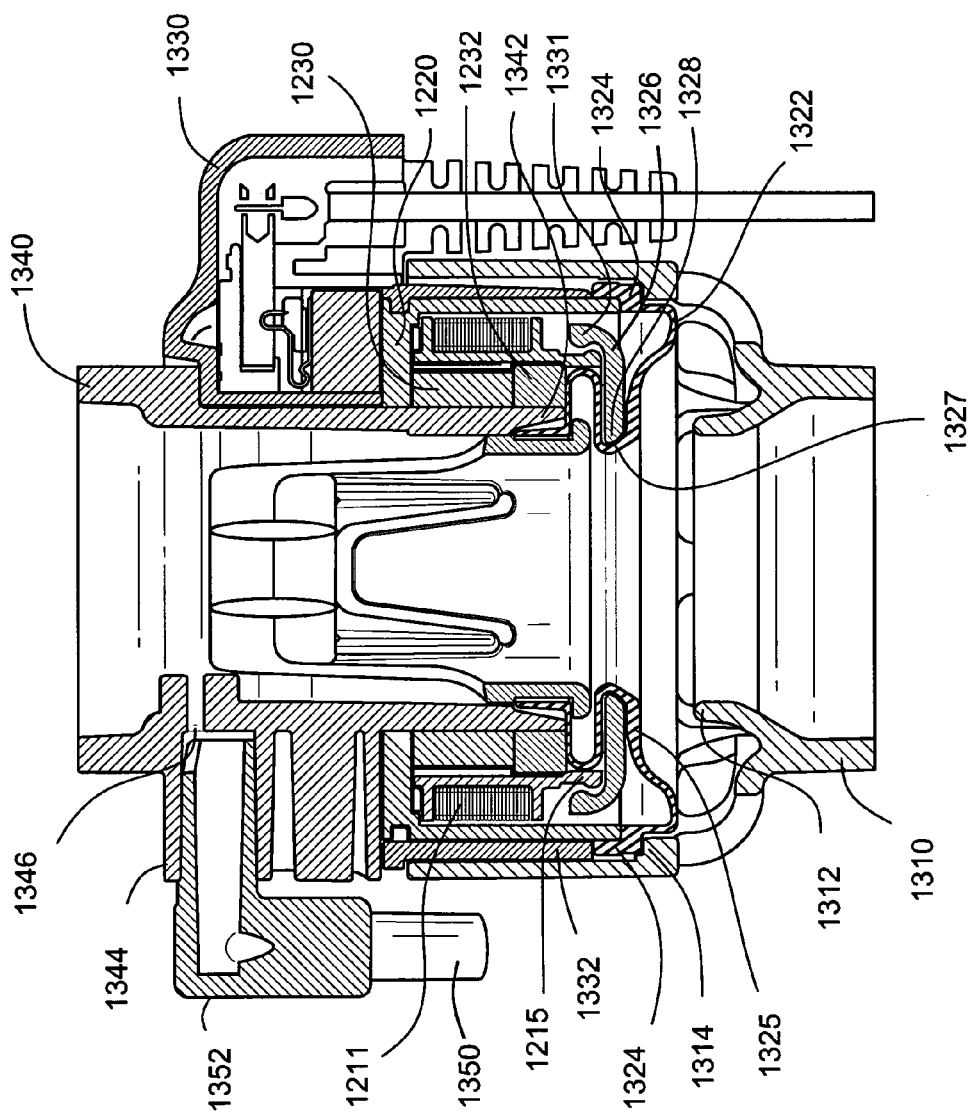
FIG. 14 is a cross-sectional view of the valve assembly shown in FIG. 12.

An assembled version of the gas regulating valve assembly 1300 is illustrated in FIG. 14. As shown therein, a protruding portion 1342 of the proximal housing 1340 extends down through the interior central aperture of the yoke 1220, magnet 1230 and pole piece 1232 of the linear actuator 1330. A portion of the membrane assembly 1320 extends into the inner cylindrical aperture within the proximal housing 1340.

Figure 13:
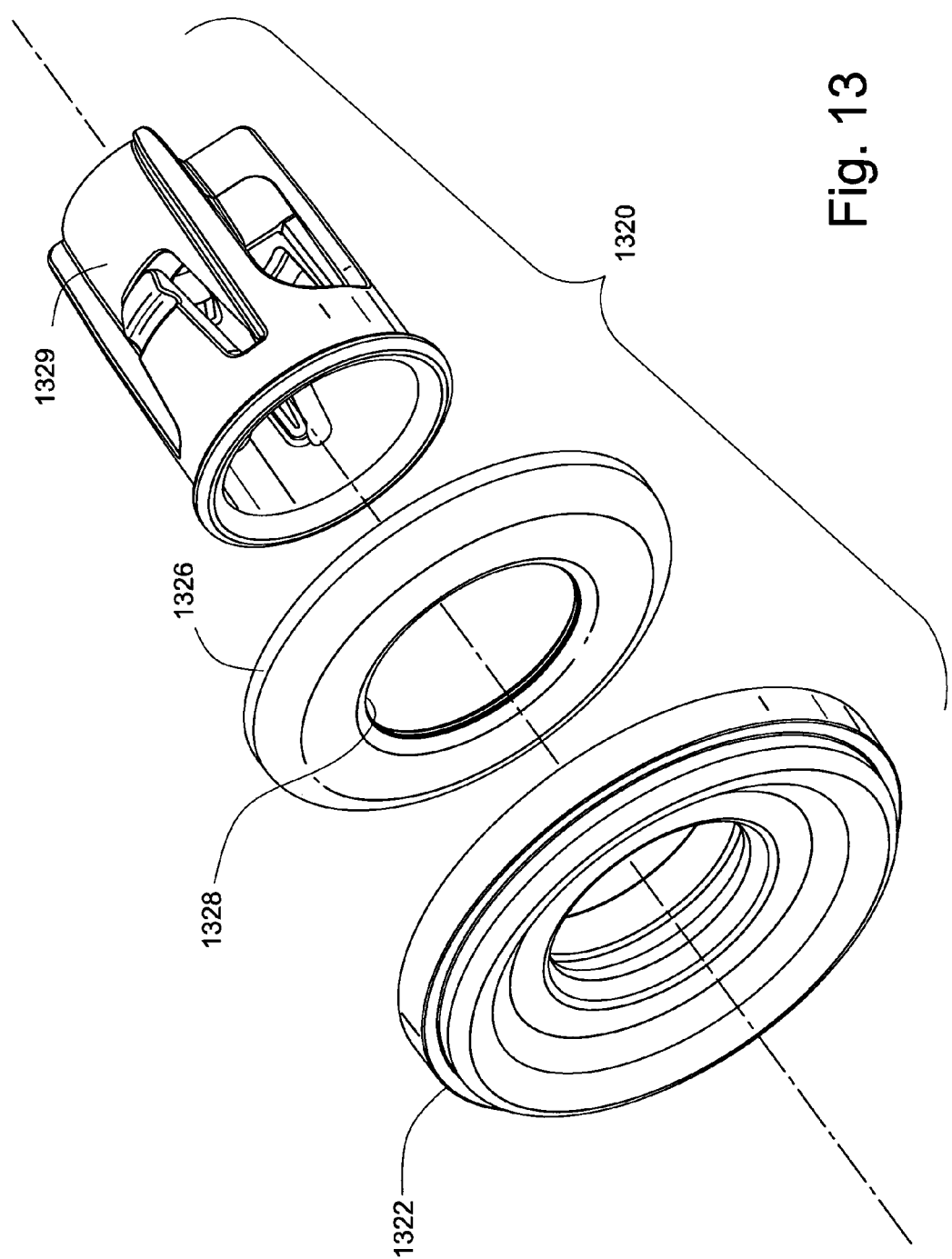
FIG. 13 is an exploded perspective view of an obstructing mechanism and a flow restrictor of the valve assembly shown in FIG. 12.

The membrane assembly 1320 is also shown in FIG. 13. As shown therein, the membrane assembly includes a clamp ring and flow restrictor 1329, an actuating ring 1326, and a membrane 1322. In an example embodiment, the membrane 1322 would include a plurality of smaller diameter and larger diameter portions which form an s-shaped or serpentine cross-section. The inner diameter 1328 of the actuating ring 1326 would be inserted into one of the smaller diameter portions of the membrane, as illustrated in FIG. 14. As mentioned above, the membrane acts as both an obstructing element and a return spring, eliminating the need for a separate return spring.

As also illustrated in FIG. 14, the distal housing 1310 would be fitted over an exterior surface of the linear actuator module 1330 and attached to the exterior surface of the proximal housing 1340. A locking mechanism would be provided to lock the distal housing 1310 onto the housing of the proximal housing 1340. In the embodiment illustrated the proximal housing 1340 comprises a latch mechanism 1348 and the distal housing comprises a complementary latch receiving mechanism 1318 that are connected to provide a regulating valve in one unit. Alternatively the distal housing 1310 may comprise the locking mechanism 1348 and the proximal housing 1340 may comprise the latch receiving mechanism 1318. Furthermore it is to be understood that alternatively other known lock mechanisms, such as clips, hooks, etc may be used to connect the proximal housing 1340 to the distal housing 1310. In addition, an exterior ring 1324 of the membrane 1322 would be trapped between a step 1314 on the distal housing 1310 and an exterior axial surface 1332 of the linear actuator assembly 1330. As a result, the membrane 1322 would form a seal between the interior of the proximal housing 1340 and the interior of the distal housing 1310. This isolates the linear actuator from the interior passage of the gas regulating valve, and thus the gas passing through the valve. Thus, the membrane has multiple functions, and acts as both an obstructing element and a return spring as described above and to isolate the linear actuator from the gas flow to prevent contamination of the linear actuator by the patient gas flow.

The actuating ring 1326 includes an interior diameter 1328 which is inserted into a reduced diameter portion 1327 of the membrane 1322. In addition, the peripheral edge of the actuating ring 1326 includes a curved portion 1331 which curves upward towards the proximal housing 1340.

The depending legs 1215 of the coil assembly 1210 of the linear actuator module 1330 bear against the flat annular surface of the actuating ring 1326. The curved portion 1331 of the actuating ring 1326 surrounds the depending legs 1215 of the coil assembly. When the coil 1211 is energized, the resulting magnetic field interacts with the magnet 1230 to cause the coil assembly to move downwards towards the distal housing 1310. The legs 1215 of the coil assembly will push against the actuating ring 1326, which causes the membrane to move downwards against a sealing face 1312 of the distal housing 1310. By controlling the signal applied to the coil 1211 of the coil assembly, one can selectively vary the gap between the sealing face 1312 of the distal housing and the corresponding sealing face 1325 on the membrane 1322.

As also shown in FIG. 14, a connector 1352 of the tube assembly 1350 would be inserted into a corresponding aperture 1344 of the proximal housing 1340. One or more apertures 1346 in the proximal housing 1340 would connect the interior of the tubes of the tube assembly 1350 to the interior of the proximal housing. This would allow the flow rate and pressure within the proximal housing to be detected. As mentioned above, in alternate embodiments, the sensor elements to detect a flow rate or pressure could also be installed at this location within the gas regulating valve.

Figure 15B:
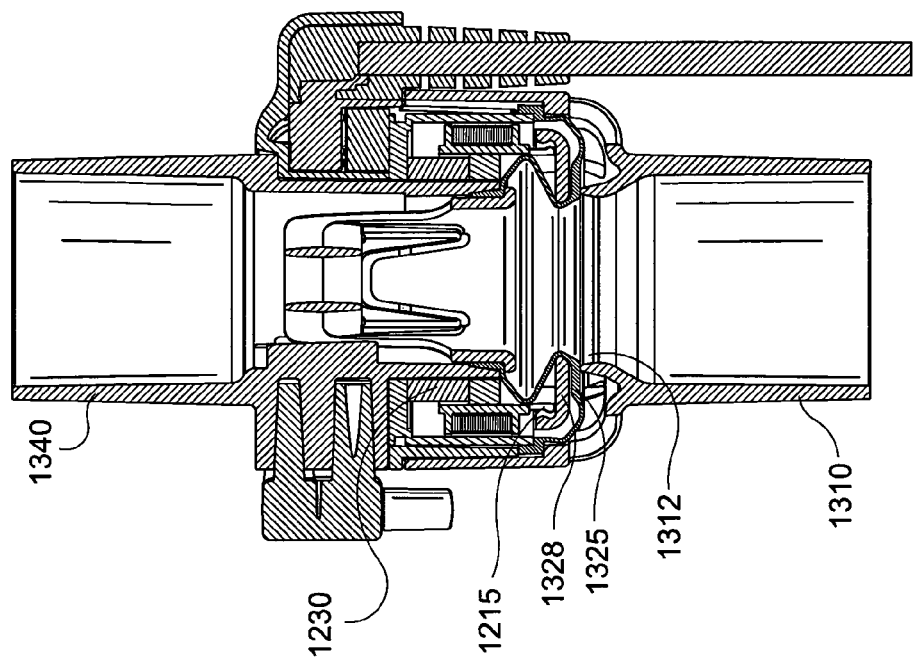
FIGS. 15*a* and 15*b* illustrate the valve assembly shown in FIG. 12 in the open and closed positions.
Figure 15A:
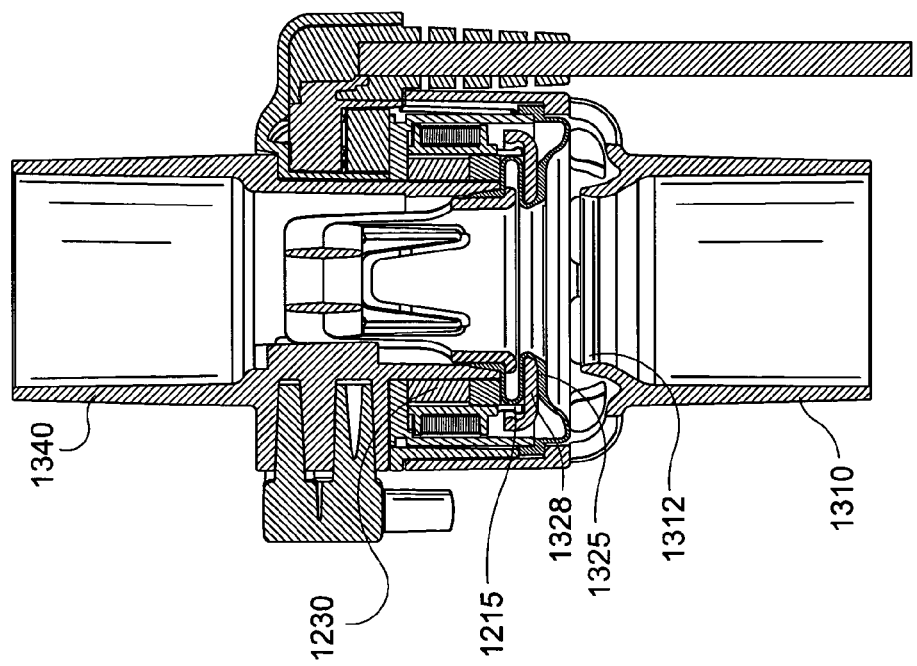

FIGS. 15a and 15b show the valve in the opened and closed positions, respectively. In FIG. 15a, the coil has been actuated so that the legs 1215 of the bobbin pull the actuating ring 1328 upward towards the proximal end. This is preferably also the position of the coil in the un-actuated or non-powered state. Thus causes the membrane 1325 to move away from the sealing face 1312 of the distal housing 1310, opening the aperture. Thus, when the valve is in the open condition, as illustrated in FIG. 15a, the patient would be able to exhale.

In FIG. 15b, the coil has been actuated so that the legs 1215 of the bobbin push the actuating ring 1328 and the membrane 1325 against the sealing face 1312 of the distal housing 1310, to thereby close the apertures. Thus seals the valve so that gas supplied from the distal end can be communicated to the patient under pressure.

If it is desirable to operate the valve to provide PEEP, then the coil would be actuated to partially open the apertures while the patient is exhaling. In this instance, the actuating ring 1328 and the membrane 1325 would be at a position between those shown in FIGS. 15a and 15b. The degree of movement of the coil could be carefully controlled in real time based on feedback from sensed pressure and flow.

Advantageously the gas regulating valve has a small size and weight making it easier and more portable to use. In one embodiment the gas regulating valve, excluding the power supply cable and connector, has a weight of approximately 40 g to 60 g, preferably 45 g to 50 g, most preferably 47 g. The maximum external diameter is approximately 40 mm to 100 mm, preferably 45 mm to 60 mm, more preferably 45 mm to 50 mm, such as 48.5 mm. The length of the gas regulating valve is approximately 60 mm to 100 mm in length, more preferably 70 mm to 85 mm, more preferably 70 mm to 80 mm, such as 77.7 mm. However, it is acknowledged that the gas regulating valve may be made in different weights, lengths and diameters as well as different shapes whilst still being within the scope of the invention.

The linear actuator advantageously concentrically manages the inspiration flow, expiration flow and actuation of the membrane, by providing movement along a single axis.

The flow restrictor 1329, as shown in FIG. 13, creates a pressure difference across the flow path. The flow restrictor 1329 could have a variety of different designs, each of which is intended to provide certain characteristics. Thus, different flow restrictors could be used in different embodiments of the valve. By selecting and installing the appropriate flow restrictor, one can customize the sensitivity of flow measurement, for example to customize the valve for different client groups such as adults and pediatrics.

In the same manner, the membrane may be tailored to have certain characteristics. For instance, some membranes might be relatively flexible, which others are relatively stiff. Also, the membrane could act as one of the elements which biases the gas regulating valve into the open position when no electricity is applied to the device.

In some instances, medical personnel could select a certain membrane, a certain actuating ring and a certain flow restrictor, and then combine them as part of the valve assembly so that the valve assembly will exhibit certain desired characteristics. In other instances, multiple different kits having these elements could be sold. Each kit would include a particular type of flow restrictor, actuating ring and membrane, and each kit would be applicable to a certain application/patient.

The membrane assembly illustrated in FIG. 13, which includes the flow regulator 1329, the actuating ring 1328 and the membrane 1322 are designed to be removed, cleaned/sterilized, and reused multiple times. Of course, the membrane and actuating ring would be relatively low cost elements which would be replaced on a periodic basis.

Operation of the valve will cause the coil to emit heat. And this heat could be beneficial. For instance, the heat of the coil could help to prevent condensation on the valve.

As explained above, a gas regulating valve as illustrated ensures that the linear actuator module is outside of the patient air path, so the linear actuator module can be reused with minimal surface cleaning. Other elements of the gas valve can either be sterilized or replaced as required. In addition, the distal housing and proximal housing, along with any pressure and flow sensing tubes, could either be sterilized or replaced as needed.

Percussive Ventilation Mode

The linear actuator described above is capable of moving rapidly in response to electrical signals. Typically, the linear actuator could move the valve between the open and closed positions as rapidly as 30 times per second or faster. When the gas regulating valve is opened and closed quickly and repeatedly, the gas regulating valve can be used in a percussive ventilation mode, which can help to mobilize secretions in a patient's airway. In addition, the rapid response of the linear actuator allows the gas regulating valve to quickly adapt to the existing operating conditions as sensed by the pressure and flow sensors. This can make it easier for a patient to breathe when connected to a breathing assistance device which includes this gas regulating valve.

Active Variable Vent

Figure 16:
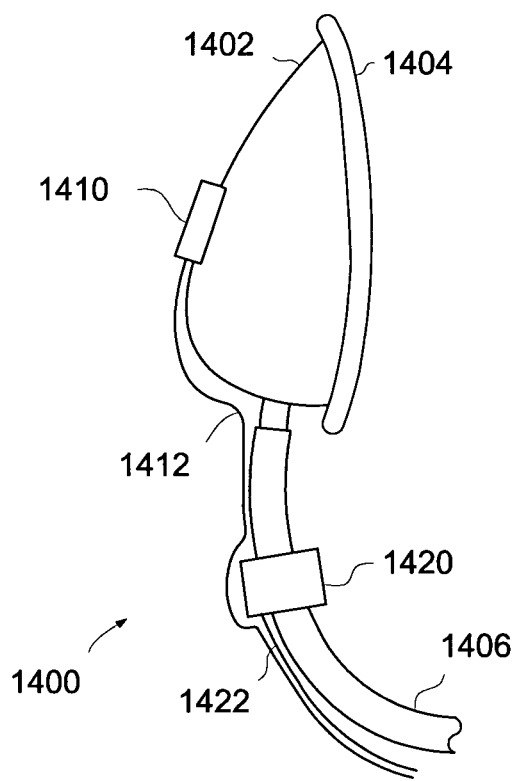
FIG. 16 illustrates a variable vented respiratory mask including a linear actuator.

A linear actuator as described above could also be used as part of a breathing assistance device that includes a variable vented respiratory mask. An example of such a device is illustrated in FIG. 16.

The variable vented respiratory mask 1400 includes a mask shell 1402, a gas supply hose 1406, and an optional gasket 1404 to ensure a good seal against a user's face. The mask 1400 also includes a flow regulator 1410, which includes a linear actuator as described above. In this instance, however, the parts of the linear actuator could be physically smaller than in the linear actuators described above, which are provided on a gas supply line. An electrical cable 1412 would connect the flow regulator 1410 to a control mechanism.

As with the mechanisms described above, a linear actuator of the flow regulator 1410 would move a blocking element into and out of engagement with an aperture in a flow passage to vary a size of the aperture that allows gas to exit the mask. Thus, the linear actuator could selectively vary the flow rate out of the mask. If a gas is supplied to the mask at a relatively constant pressure, the linear actuator could control the size of the aperture to ensure that a relatively constant pressure is maintained within the mask while the user inhales and exhales. Thus, this type of a mask could be particularly useful in a CPAP system. In some embodiments, the linear actuator could be actuated by a controller that monitors the internal pressure within the mask.

As with the valves described above, the elements of the linear actuator in the flow regulator 1410 could be completely isolated from the gas flow path. As a result, it would be possible to re-use the linear actuator with different patients without the need to sterilize the linear actuator itself. For instance, the linear actuator could be installed in a first flow regulator 1410 of a first user's mask, and then the linear actuator could be removed from that mask and installed into a flow regulator 1410 of a second user's mask without sterilizing the linear actuator.

A mask as illustrated in FIG. 16 might also be used in a system which includes a flow valve 1420 having a linear actuator as described above in the gas supply line 1406. The linear actuator in the flow valve 1420 would also be connected to a controller by an electrical cable 1422. In this type of a system, the linear actuator of the valve 1420 in the gas supply line and the linear actuator of the flow regulator 1410 of the mask could be actuated by the same controller. And by selectively actuating the two linear actuators, the controller could achieve extremely good control over the flow of gas into and out of the mask.

Retrofit to Existing Devices

The gas regulating valve described above is able to control the delivery of a gas to a patient with a relatively compact and simple structure. As such, the valve could be retrofitted onto existing ventilator and breathing assistance devices such as those illustrated in FIGS. 1*a*-1*d* and 2*a*-2*d*. In particular, it may be possible to retrofit one of the gas regulating valves described above into the embodiment as shown in FIGS. 2*a*-2*d*, to replace the proximal valve which was previously operated based on air pressure. This would eliminate the need for a separate air tube 23 to control the opening and closing of the gas regulating valve, and it would likely simplify the control structure. These changes to the device shown in FIGS. 2*a*-2*d* would reduce the size of the device, and possibly make the device more easily portable. Moreover, a gas regulating valve with an electrically controlled linear actuator may be capable of opening and closing more quickly and precisely.

Breathing Assistance Systems with Relocated and/or Multiple Valve Assemblies

The breathing assistance system illustrated in FIG. 3 includes a single gas regulating valve 32 that controls the flow of air delivered to the patient, and the gas regulating valve is located adjacent to the patient P.

In some embodiments, the gas source S of the breathing assistance system shown in FIG. 3 delivers humidified gas or humidified atmospheric air to provide therapy to a patient. The humidified gas is typically output from the gas source S at a temperature above normal ambient temperatures. The humidified gas travels through the gas delivery lines and the gas regulating valve before reaching the patient. As it travels along this flow path, the humidified gas will tend to cool down and condense. As a result, some of the water vapor in the humidified gas may condense and collect within the gas supply lines. The presence of condensed water can interfere with providing therapy, and can lead to patient infection due to microbial growth.

In some breathing assistance devices that deliver humidified gas, therapy is delivered only intermittently. For instance, the breathing assistance device may be designed to deliver therapy only when required, and to turn off when therapy is not required. Therapy may only be provided when snoring is detected, and when snoring stops, the therapy may be discontinued. In other instances, the breathing assistance device may be configured to provide therapy only when the patient is in sleep stage 4, or only when the patient is in sleep stages 3 or 4. At all other times, no therapy would be provided.

In other instances, a breathing assistance device may be configured to provide therapy on a periodic basis. For instance, the breathing assistance device may be configured to deliver therapy for a first predetermined period of time, and to then discontinue therapy for a second predetermined period of time. This on/off cycle can continue indefinitely.

When a breathing assistance device that delivers humidified gas is switched on and off, during the off times, any humidified gas that remains in the gas supply lines will tend to cool, and the water vapor in the gas may condense and collect in the gas supply pipes. As noted, the presence of condensed water in the gas supply lines can reduce the effectiveness of subsequent treatment cycles, and it poses a risk of infection due to microbial growth.

With a system as illustrated in FIG. 3, when treatment has ended, or has been temporarily discontinued, the gas regulating valve will revert to an "open" position, which allows a patient to breathe, and which also opens the end of the gas delivery line adjacent the patient to the atmosphere. However, because the only opening to the atmosphere is at the patient side, it is difficult for all of the water vapor in the humidified air in the gas delivery lines to escape.

Figure 17:
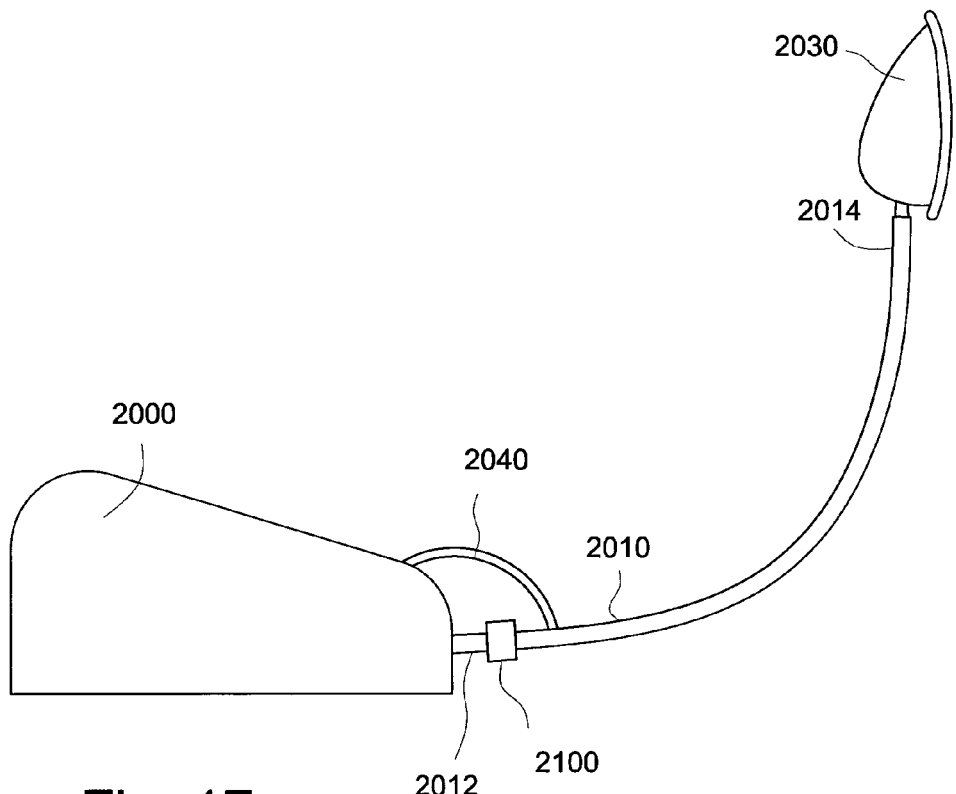
FIG. 17 is a schematic representation of a breathing assistance device which makes use of a gas regulating valve adjacent a gas source.

FIG. 17 illustrates a first alternate embodiment in which the gas regulating valve has been re-located from the patient side to the gas source side. In this embodiment a gas source 2000 provides humidified gas or humidified atmospheric air through an output pipe 2012. A distal gas regulating valve 2100 is connected to the output pipe 2012. The distal gas regulating valve 2100 is also coupled to a first end of a gas supply line 2010 which leads to a patient interface 2030. The patient interface 2030 may be any type of patient interface unit, such as a nasal mask, full face mask, nasal prongs, or a nasal cannula such as the ones used to provide open CPAP therapy. The distal gas regulating valve 2100 can be one of the linear actuated gas regulating valves as illustrated in FIGS. 12-15*b*.

A system as illustrated in FIG. 17 could be used as an OpenCPAP system, in which the gas regulating valve is attached to the outlet of a humidifier. In some embodiments, a supplemental gas supply line 2040 may also deliver predetermined amounts of an additional gas, such as oxygen, into the gas supply line 2010. The supplemental gas supply line 2040 could be coupled to the gas supply line 2010 on the patient side of the distal gas regulating valve 2100, as illustrated in FIG. 17. In alternate embodiments, the supplemental gas supply line 2040 could be coupled to the output pipe 2012.

So long as the distance between the gas source 2000 and the patient interface 2030 is short, it is possible to re-locate the gas regulating valve to a position adjacent the gas source, and doing so helps to reduce the above-discussed problems with condensation. During treatment cycles, the distal gas regulating valve 2100 would be closed, or at least partially closed. Therefore the therapeutic airflow passes through the distal gas regulating valve 2100 and through the delivery tube 2010 to the patient interface.

When treatment is discontinued, the distal gas regulating valve 2100 would open the gas delivery tube 2010 to the atmosphere and no gas would flow to the patient interface. Thus, the air delivery tube 2010 is decoupled from the gas source. The gas regulating valve may be used to control the delivery of the treatment only at desired times or when required, as described above.

In some embodiments, the gas source may also be turned off or inactivated at the same time that the distal gas regulating valve 2100 is opened to the atmosphere to discontinue treatment. This would also result in no flow through the humidifier/gas source, which would result in less cooling of the heated water in the humidifier. Consequently, when therapy is to be re-started, the temperature of the water in the humidifier is substantially maintained such that effective treatment may be recommenced quickly. There is a reduction in or no delay due to reheating of the water in the humidifier. When treatment is to be restarted, the gas source is turned on or reactivated and the distal gas regulating valve 2100 is closed, or at least partially closed, to the atmosphere.

When treatment is discontinued, and the patient is breathing through the gas delivery tube 2010, the patient's respiration would flush out any moisture remaining in the gas delivery tube from the treatment cycle that just ended. Thus, placing the only gas regulating valve at the gas source 2000 side of the gas delivery tube 2010 helps to prevent condensation within the gas delivery tube. The gas regulating valve 2100 provides a vapor suspension system that eliminates or at least reduces the occurrence of condensation within the air delivery tube and isolates hot water in the humidifier. The saturated vapor present in the system at the time treatment is interrupted is vented out rapidly with the patient providing the "flushing" circuit. Creating a draft through the air delivery tube allows the tube to dry out and prevents condensation.

In one embodiment this system may be used with an Open CPAP device such as the devices described in the Applicant's co-pending PCT application PCT/AU2009/000671, filed 28 May 2009, and published as WO 2009/146484. In Open CPAP systems, the patient interface may include a nasal cannula. In other embodiments, the system may be used with a CPAP system using a mask or nasal prongs.

Figure 18:
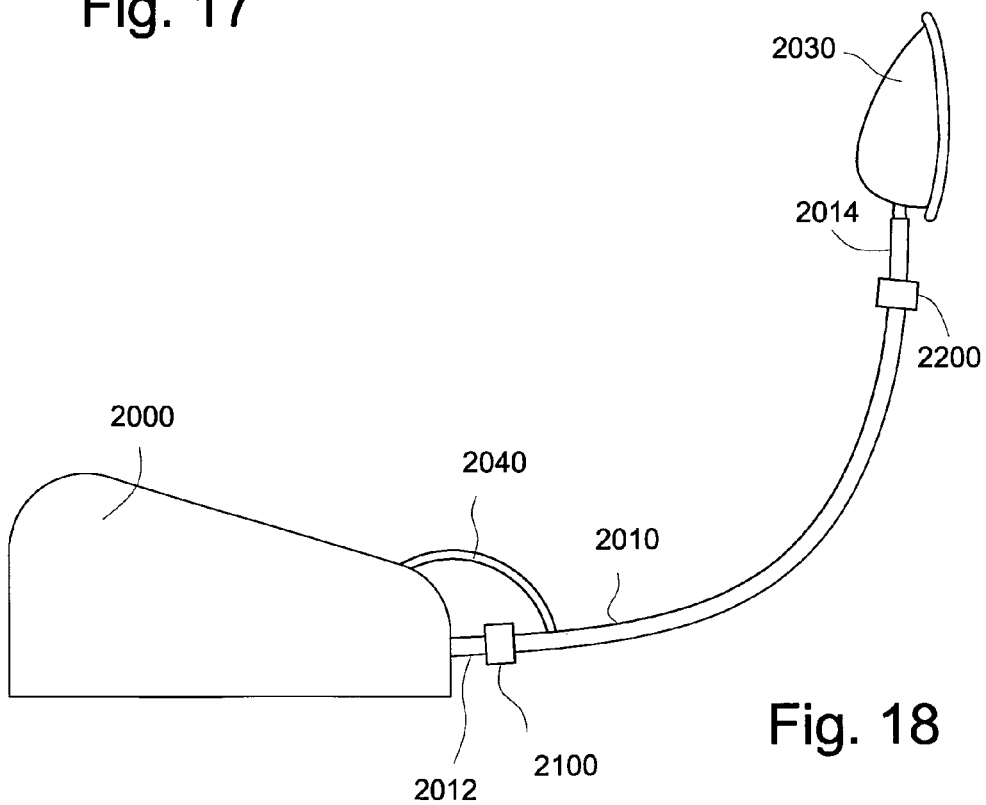
FIG. 18 is a schematic representation of a breathing assistance device which makes use of two gas regulating valves located at opposite ends of a gas delivery tube.

FIG. 18 illustrates another alternate embodiment where a gas regulating valve is located at both ends of the gas delivery tube 2010. In this embodiment, a proximal gas regulating valve 2200 is connected between a second end of the gas delivery tube and the patient interface.

The breathing assistance device illustrated in FIG. 18 is configured such than when therapy is stopped, both the distal gas regulating valve 2100 and the proximal gas regulating valve 2200 default to the open position. This means that both ends of the gas supply line 2010 are open to the atmosphere, which helps to more rapidly dissipate and evaporate any moisture left in the gas supply line 2010 when therapy has been discontinued.

Some breathing assistance devices as illustrated in FIGS. 3, 17 and 18 include heated gas delivery tubes that are designed to promote drying and to reduce undesirable condensation. If only a proximal gas regulation valve were provided, as illustrated in FIG. 3, and if the patient interface side is lower than the gas source, heating of the gas delivery lines may not be effective in flushing out moist air between treatment cycles. Under those circumstances, heating the moist air within the gas delivery lines would cause the moist air to rise toward the gas source side where it cannot escape the gas delivery lines.

However, when both a distal gas regulation valve 2100 and a proximal gas regulation valve 2200 are provided, it will not matter which end is higher. Heating of the gas delivery lines between treatment cycles, while both gas regulating valves are open, will cause the moist gas within the gas delivery lines to rise toward and escape from whichever end is higher.

In some embodiments of the breathing assistance devices illustrated in FIGS. 17 and 18, the distal gas regulating valve 2100 may also include means for sealing off the output pipe 2012 when treatment is being discontinued. In these embodiments, when the distal gas regulating valve 2100 is placed in the "open" position, the gas delivery line 2010 would be open to the atmosphere and the output pipe 2012 would be sealed. Sealing the output pipe would help to prevent any heated gas within the gas source 2000 from escaping during a non-treatment period. Sealing the output pipe 2012 would also help to keep any heated water or liquid within the gas source 2000 at a high temperature. When treatment is later re-started, the gas source could immediately be delivering humidified gas, as there would be no delay while the gas source 2000 heats the liquid up to a temperature required to provide the humidified gas.

In all of the embodiments described above, the gas regulating valves and the gas source preferably would be linked such that if any of the elements fail, all elements would be turned off. As explained above, when the gas regulating valves are turned off, they simply default to the open position.

Breathing Assistance Systems with Expiratory Flow Measurement

Figure 19:
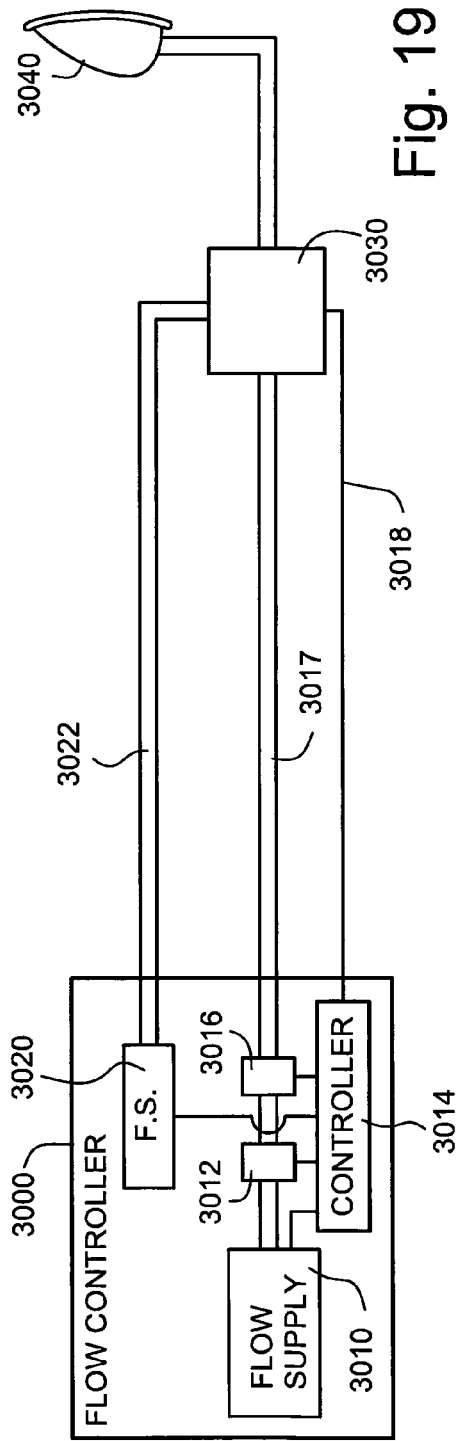
FIG. 19 is a schematic diagram of elements of a breathing assistance system that includes a linear actuated gas regulating valve.

FIG. 19 illustrates a breathing assistance device. The device includes a flow controller 3000, which supplies a flow of gas to a patient interface 3040 via a gas regulating valve 3030. The gas regulating valve could be a linear actuated gas regulating valve as illustrated in FIGS. 6a-15b, and as described above.

The flow controller 3000 includes a flow generator 3010 that generates a flow of a treatment gas, which would typically be atmospheric air. A non-return valve 3012 is operable to selectively block an output line connected to the flow generator 3010. Also, a supply line pressure sensor 3016 senses the pressure in a gas supply line 3017 leading to the gas regulating valve 3030. The flow generator 3010, the non-return valve and the supply line pressure sensor 3016 are all coupled to a controller 3014.

The gas regulating valve opens and closes in response to a signal provided from the controller 3014 via a valve driver line 3018.

Also, two bypass flow conduits 3022 are coupled between the gas regulating valve 3030 and a flow sensor 3020 in the flow controller. When a patient exhales, a small portion of the expiratory flow passes down one bypass flow conduit, passes across the flow sensor 3020, and flows back down the other bypass flow conduit back to the gas regulating valve. A signal generated by the flow sensor 3020, which is indicative of the expiratory flow, is communicated to the controller 3014.

The breathing assistance device is configured such that when a patient is inhaling, the non-return valve 3012 is open, and the gas regulating valve 3030 is closed. As a result, pressurized gas flows from the flow generator 3010 through the gas supply line 3017, through the gas regulating valve 3030, and into the patient interface 3040. When the patient is exhaling, the controller causes the non-return valve 3012 to close, and the gas regulating valve 3030 to at least partially open. As a result, compressed gas does not flow down the gas supply line 3017, and the patient is allowed to exhale through the opened gas regulating valve 3030. In some instances, the degree to which the gas regulating valve is opened is selectively varied by the controller 3014 to maintain a desired pressure throughout the exhalation process.

In many instances, to provide proper treatment to the patient, it is desirable to measure the patient's expiratory flow. In the embodiment illustrated in FIG. 19, the expiratory flow is measured by the flow sensor 3020. In alternate embodiments, the controller 3014 may determine the expiratory flow based on a signal from the flow sensor 3020.

Providing the bypass flow conduits and the flow sensor 3020 adds considerable bulk and cost to the system. Also, arranging the bypass flow conduits can be inconvenient. The fact that a portion of the patient's exhalation flows through the bypass flow conduits 3022 and through the flow sensor 3020 means that the exhalation resistance for the patient may be larger than it otherwise would be. In addition, because the patient's exhalations are communicated to the flow sensor, the flow sensor 3020 becomes contaminated, and it is necessary to replace the flow sensor 3020 for each new patient that uses the system.

Figure 20:
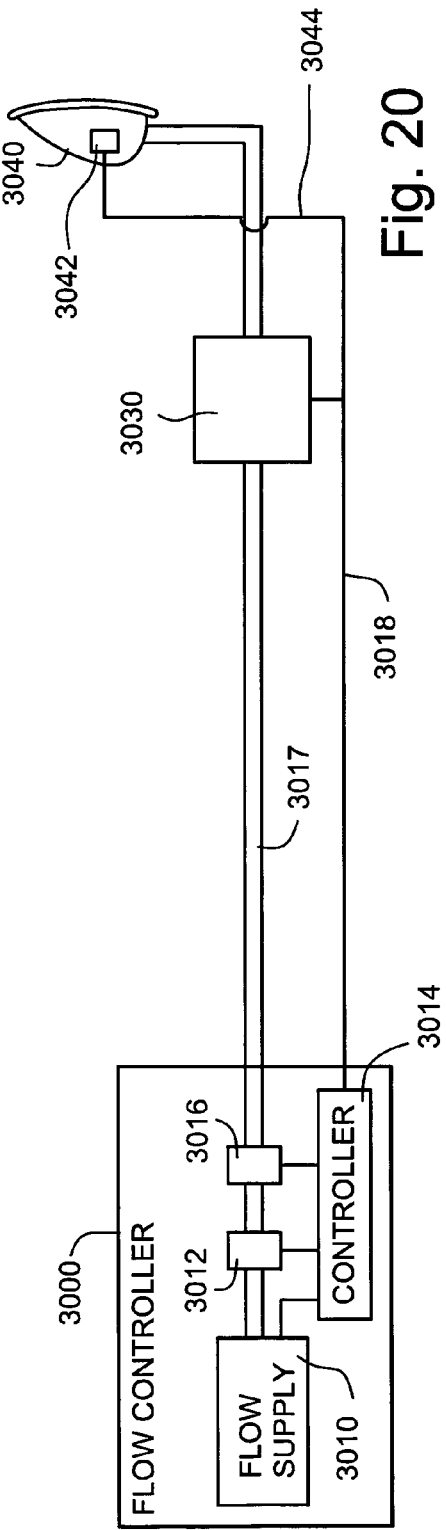
FIG. 20 is a schematic diagram of elements of another embodiment of a breathing assistance system which makes use of a linear actuated gas regulating valve.

Another approach to sensing the patient's expiratory flow can be accomplished with a system as illustrated in FIG. 20. In this embodiment, the flow sensor 3020 and the bypass flow conduit are eliminated. However, a pressure sensor 3042 is added to the patient interface. The pressure sensor can be an electronic sensor that derives power from the power line running to the gas regulating valve 3030, and which sends a sensor signal to the controller 3014 along one or more additional wires that are run with the valve driver line. In alternate embodiments, the pressure sensor could be located on the proximal side of the gas regulating valve 3030.

As explained above, during expiration, the gas regulating valve 3030 will be at least partially open, and the patient will exhale through the opening to the atmosphere. The expiratory flow can be calculated based on the pressure drop that occurs between the patient interface and the atmosphere, and the impedance offered by the gas regulating valve 3030. If Pmask is the pressure on the patient side of the gas regulating valve, and Patm is the atmospheric pressure, The general formula would be:

Expiratory Flow=(Pmask−Patm)/Valve Impedance

As explained above, the opening provided by the gas regulating valve would be selectively varied by the controller 3014 to maintain a desired pressure during exhalation. As a result, the valve impedance would vary during the exhalation.

As explained above, a gas regulating valve as illustrated in FIGS. 6a-15b is opened and closed by applying a signal to a coil. If no signal is applied to the coil, the valve remains open. The greater the value of the signal applied to the coil, the more the valve will close. As a result, the amount of flow resistance provided by the gas regulating valve is proportional to the drive signal applied to the gas regulating valve. The greater the value of the signal, the more the valve closes, and the greater the flow resistance.

If the valve impedance was linearly proportional to the value of the signal applied to the valve by the controller 2014, one could simply use the value of the drive signal, along with a correction constant as a substitute for the actual valve impedance. If the correction factor was K, the equation used to calculate the expiratory flow could be expressed as:

Expiratory Flow=(K)*(Pmask−Patm)/Valve Drive Signal

In fact, the valve impedance is not linearly proportional to the value of the drive signal. However, after conducting experimentation, it is possible to create a lookup table that will provide the valve impedance for various different values of the valve drive signal. And the valve impedance obtained through the lookup table could then be used, along with the pressure differential, to calculate the expiratory flow.

Also, if the pressure sensor 3042 used in the patient interface 3040 or on the patient side of the gas regulating valve indicates the pressure on the patient side of the gas regulating valve relative to atmospheric pressure, the portion of the equation calling for the pressure differential between Pmask and Patm is given simply by the output of the pressure sensor 3042.

In view of all of the foregoing, it is possible to closely estimate the expiratory flow using the value of the signal applied to the gas regulating valve, and the value of the signal output from the pressure sensor 3042.

In alternate embodiments, the pressure on the patient side of the gas regulating valve 3030 could also be sensed by having a single bypass conduit 3022 coupled to an aperture on the patient side of the gas regulating valve. This single bypass flow conduit could lead to a pressure sensor on the flow controller 3000.

During exhalation, the non-return valve 3012 should be closed, and no positive air pressure should be applied to the distal side of the gas regulating valve. However, if a particular embodiment of a breathing assistance device called for positive air pressure to be applied by the flow generator 3010 during expiration, the value of that pressure would be provided by the supply line pressure sensor 3016. Thus, the value of that pressure could be taken into account in calculating the expiratory flow.

Similar techniques could be used to estimate patient inspiratory flow. During patient inspiration, the gas regulating valve 3030 will be closed, and gas will be flowing from the flow supply 3010, through the gas supply line 3017, through the gas regulating valve 3030 and into the patient interface 3040. If Pfg is the pressure of the gas as supplied by the flow supply, Pmask is the pressure on the patient side of the gas regulating valve, and Total Impedance is the impedance provided by the gas supply line 3017 and the gas regulating valve 3030, then the inspiratory flow is given the equation:

Inspiratory Flow=(Pfg−Pmask)/Total Impedance

Because a pressure sensor 3016 is provided at the flow supply 3010, Pfg would be known. Likewise, the pressure on the patient side of the gas regulating valve 3030 would be sensed by a pressure sensor on the patient interface or the patient side of the gas regulating valve, so Pmask would also be known. As also noted above, the pressure on the patient side of the gas regulating valve might also be sensed by a pressure sensor on the flow controller 3000 that is coupled to the patient side of the gas regulating valve 3030 by a bypass conduit.

The total impedance of the system would include the impedance provided by the gas regulating valve 3030 and the elements located between the flow supply 3010 and the gas regulating valve, most notably, the gas supply line 3017. The impedance would vary in a non-linear fashion with respect to the supply pressure. Thus, experimentation could be conducted to create a look up table that indicates the total impedance as a function of the gas supply pressure Pfg. Alternatively, the look up table could indicate the total impedance as a function of the pressure on the patient side of the gas regulating valve.

Once Pfg, Pmask and Total Impedance are determined, as described above, it is possible to estimate the inspiratory flow.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

Furthermore, each individual component of any given assembly, one or more portions of an individual component of any given assembly, and various combinations of components from one or more embodiments may include one or more ornamental design features.

In addition, while the invention has particular application to patients who require a ventilator, or who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A linear actuator for a gas regulating valve, comprising:
a housing;
a yoke mounted inside the housing;
a coil assembly inserted within the yoke;
a magnetic element inserted within the coil assembly;
a circuit assembly coupled to an axially facing outer surface of the yoke;
a central aperture radially inner to the magnetic element and extending axially through the housing; and
a fixed flow restrictor placed within the central aperture;
wherein the central aperture is adapted to receive a gas flow path extending through the fixed flow restrictor;
wherein the coil assembly includes a bobbin having a wire coil wound thereon and wire aligning structures adapted to facilitate attachment of ends of the wire coil to the circuit assembly through apertures provided in the yoke;
wherein the coil assembly is adapted to move in an axial and a linear direction within the yoke in response to electro-magnetic forces applied by the magnetic element;
wherein the fixed flow restrictor is configured to create a pressure difference across the gas flow path.

2. The linear actuator of claim 1, wherein the central aperture is configured to allow a gas flow to travel through the central aperture without obstruction.

3. The linear actuator according to claim 1, wherein the yoke comprises a circumferential wall a central yoke aperture and the apertures provided in yoke radially outer to the central yoke aperture.

4. The linear actuator according to claim 3, wherein the apertures provided in the yoke radially outer to the central yoke aperture are continuous with the central yoke aperture.

5. The linear actuator according to claim 1, further comprising a removably installed membrane assembly arranged adjacent to the yoke.

6. The linear actuator according to claim 5, wherein movement of the coil assembly is arranged to deform the removably installed membrane assembly.

7. The linear actuator according to claim 1, wherein the fixed flow restrictor is placed interior to the yoke.

8. The linear actuator according to claim 1, wherein the coil assembly is configured to move relative to the fixed flow restrictor.

9. A linear actuator for a gas regulating valve, comprising:
a housing;
a yoke mounted inside the housing;
an annular bobbin that is movably mounted inside the yoke and that has first and second arms that extend axially from a location around a circumferential body of the bobbin, wherein a wire coil is wrapped around the bobbin and respective first and second ends of the wire coil are coupled to the first and second arms of the bobbin;
a flexible circuit assembly having a central portion that is attached to the yoke and first and second extensions that extend from the central portion and that are attached to the first and second arms of the bobbin, respectively, wherein first and second electrical contacts are formed on the central portion, the first and second electrical contacts being coupled, respectively, to first and second ends of the wire coil;
a fixed flow restrictor placed within a central aperture of the housing and configured to create a pressure difference across a gas flow path;
and a magnet that is attached to the yoke.

10. The linear actuator according to claim 9, wherein the fixed flow restrictor is placed interior to the yoke.

11. The linear actuator according to claim 9, wherein annular bobbin is configured to move relative to the fixed flow restrictor.

12. A gas regulating valve, comprising:
a generally linear actuator having a central passageway extending therethrough;
a first housing portion configured to be attached to a gas delivery tube;
a second housing portion configured to be attached to a patient interface, wherein one of the first and second housing portions extends at least partially through the central passageway of the linear actuator; and
a removably installed membrane assembly that is coupled between the first and second housing portions such that a gas passing through the first and second housing portions and through the membrane assembly is isolated from the linear actuator; and
a fixed flow restrictor arranged within the central passageway such that the gas has a flow which must pass through the fixed flow restrictor in use,
wherein the fixed flow restrictor is configured to create a pressure difference across the flow.

13. The gas regulating valve according to claim 12, wherein the fixed flow restrictor is placed interior to the linear actuator.

14. The gas regulating valve according to claim 12, wherein the linear actuator is configured to move relative to the fixed flow restrictor.

15. A method of manufacturing a gas regulating valve, comprising:
inserting a first end of a first housing portion through a linear actuator to form a first section of a central gas passageway;
inserting a removably installed membrane assembly into the first end of the first housing portion and coupling a first end of the membrane assembly to the first housing portion to form a second section of the central gas passageway;

placing a fixed flow restrictor within the central gas passageway such that a flow path must pass through the fixed flow restrictor in use; and attaching a second housing portion to the first housing portion, wherein the second housing portion provides a third section of the central gas passageway adjacent a second end of the membrane assembly such that the central gas passageway is formed through the first housing portion, the membrane assembly and the second housing portion, the central gas passageway being isolated from the linear actuator, wherein the fixed flow restrictor is configured to create a pressure difference across the flow path.

16. The method according to claim 15, wherein the fixed flow restrictor is placed interior to the linear actuator.

17. The method according to claim 15, wherein the linear actuator is configured to move relative to the fixed flow restrictor.

18. A method of manufacturing a linear actuator, comprising: inserting a hollow annular bobbin having a wire coil wound thereon inside a hollow yoke, the bobbin having a first and a second axially protruding arm, both of which extend through the yoke; coupling a first and second end of the wire coil to the first and second axially protruding arm of the bobbin, respectively, the first and second axially protruding arms of the bobbin protruding from the annular bobbin around its circumference; attaching a central portion of a flexible circuit assembly to an axial face of the yoke, the flexible circuit assembly having first and second extensions protruding from the central portion; coupling first and second ends of the wire coil to the first and second extensions of the flexible circuit assembly; inserting a hollow magnet inside the bobbin; inserting a fixed flow restrictor within a central aperture, the fixed flow restrictor configured to create a pressure difference across a gas flow path; and attaching the magnet to the yoke.

19. The method according to claim 18, wherein the fixed flow restrictor is placed interior to the yoke.

20. The method according to claim 18, wherein the annular bobbin is configured to move relative to the fixed flow restrictor.

21. A method of treating a patient with a breathing assistance device which includes a gas supply, a patient interface, a gas supply line coupling the gas supply and the patient interface, and a gas regulating valve with a removably installed membrane assembly that controls a flow of the gas from the gas supply to the patient interface, wherein the gas regulating valve includes a linear actuator comprising a magnet and a coil, the magnet and the coil being arranged radially outer to a housing defining a flow path of the gas within the device, the flow path including passing through a fixed flow restrictor, the fixed flow restrictor configured to create a pressure difference across the flow path, the method comprising:

sensing a gas pressure in one of the supply line and the patient interface, the gas supply passing through the fixed flow restrictor; and sending a control signal which is based on the sensed gas pressure to the linear actuator of the gas regulating valve to cause linear movement of the coil of the linear actuator, wherein the linear movement of the coil causes an obstruction member of the gas regulating valve to move.

22. The method of claim 21, wherein the coil moved in response to a control signal surrounds the patient airway, but is sealed off from contact with the patient airway.

23. The method of claim 21, wherein the coil of the linear actuator is coupled to a stationary yoke of the linear actuator by a flexible circuit assembly, and wherein when the control signal causes the coil to move, the flexible circuit assembly flexes to accommodate movement of the coil.

24. The method of claim 21, wherein the actuator is sealed off from the flow path of the gas.

25. The method of claim 21, wherein the magnet and the coil assembly are sealed off from the path of the gas.

26. The method according to claim 21, wherein the fixed flow restrictor is placed interior to the linear actuator.

27. The method according to claim 21, wherein the linear actuator is configured to move relative to the fixed flow restrictor.

28. A method of treating a patient with a breathing assistance device which includes a patient interface with a linear actuator that controls a size of an exhalation vent of the patient interface, the exhalation vent being configured to be closed by a removably installed membrane assembly, wherein the linear actuator comprises a magnet and a coil, the magnet and the coil being arranged radially outer to a housing defining a flow path of the gas within the device, the flow path including passing through a fixed flow restrictor, a gas supply and a supply line coupling the gas supply and the patient interface, the fixed flow restrictor configured to create a pressure difference across the flow path, the method comprising:

arranging the flow path of the gas supply to pass through the fixed flow restrictor;

sensing a gas pressure in at least one of the gas supply line and the patient interface; and sending a control signal which is based on the sensed gas pressure to the linear actuator to cause linear movement of the coil of the linear actuator, wherein the linear movement of the coil causes an obstruction member of the exhalation vent to move.

29. The method of claim 28, wherein the control signal causes movement of a cylindrical coil that surrounds a patient airway through the exhalation vent, but which is sealed off from contact with the patient airway.

30. The method of claim 28, wherein the coil of the linear actuator is coupled to a stationary yoke of the linear actuator by a flexible circuit assembly, and wherein when the control signal causes the coil to move, the flexible circuit assembly flexes to accommodate movement of the coil.

31. The method according to claim 28, wherein the fixed flow restrictor is placed interior to the linear actuator.

32. The method according to claim 28, wherein the linear actuator is configured to move relative to the fixed flow restrictor.

33. A breathing assistance device, comprising:
a gas supply;
a patient interface;
a gas supply line coupling the gas supply and the patient interface;
a fixed flow restrictor; and
a gas regulating valve coupled between the gas supply and the gas supply line, wherein the gas regulating valve controls a flow of the gas from the gas supply to the patient interface, and wherein the gas regulating valve includes a removably installed membrane assembly and a linear actuator comprising a magnet and a coil assembly, the magnet and the coil assembly being arranged radially outer to a housing defining a flow path of the gas within the device, the flow path including passing through the fixed flow restrictor,
wherein the fixed flow restrictor is configured to create a pressure difference across the flow path.

34. The breathing assistance device of claim 33, wherein the gas supply supplies humidified gas.

35. The breathing assistance device of claim 33, wherein when the gas regulating valve is in a closed position, the gas regulating valve couples an output line of the gas supply into the gas supply line, and wherein when the gas regulating valve is in an open position, the gas regulating valve opens the gas supply line to the atmosphere.

36. The breathing assistance device of claim 35, wherein when the gas regulating valve is in the open position, the gas regulating valve closes the output line of the gas supply.

37. The breathing assistance device of claim 33, wherein the gas regulating valve comprises a distal gas regulating valve, and further comprising a proximate gas regulating valve that couples the patient interface to the gas supply line.

38. The breathing assisting device according to claim 33, wherein the fixed flow restrictor is placed interior to the linear actuator.

39. The breathing assisting device according to claim 33, wherein the linear actuator is configured to move relative to the fixed flow restrictor.

40. A method of calculating a patient's expiratory flow when the patient is using a breathing assistance device that includes a patient interface that is coupled to a gas regulating valve located between an interior of the breathing device and atmosphere, the gas regulating valve including a removably installed membrane assembly, wherein a control signal is applied to the gas regulating valve to control a flow through the gas regulating valve, the flow passing through a fixed flow restrictor, the method comprising:
passing the flow of gas through the fixed flow restrictor, the fixed flow restrictor configured to create a pressure difference across the flow;
determining a pressure difference between a pressure within the patient interface and atmospheric pressure while the patient is expiring;
determining a value of the control signal applied to the gas regulating valve located between the interior of the breathing device and atmosphere while the patient is expiring; and
calculating the patient's expiratory flow based on the determined pressure difference and the determined value of the control signal.

41. The method according to claim 40, wherein a linear actuator is configured to move relative to the fixed flow restrictor.

42. A breathing assistance device, comprising:
a gas supply;
a gas supply line coupled to the gas supply;
a patient interface;
a pressure sensor that senses a pressure within the patient interface;
a gas regulating valve coupled between the gas supply line and the patient interface, wherein the gas regulating valve includes a movable obstruction member that moves between a closed position at which the gas regulating valve couples the gas supply line to the patient interface and an open position at which the gas regulating valve couples the patient interface to the atmosphere, the gas regulating valve including a removably installed membrane assembly, the gas regulating valve being configured to require a flow path through the gas regulating valve to pass through a fixed flow restrictor, the fixed flow restrictor configured to create a pressure difference across the flow path; and
a controller that is coupled to the pressure sensor and the gas regulating valve, wherein the controller sends a control signal to the gas regulating valve that controls a degree to which the obstruction member moves from the open position toward the closed position, and wherein the controller calculates an expiratory flow of the patient when the patient is exhaling based upon a pressure within the patient interface, as sensed by the pressure sensor, and a value of the control signal sent to the gas regulating valve.

43. The breathing assistance device of claim 42, wherein the controller determines an impedance of the gas regulating valve based on the value of the control signal sent to the gas regulating valve, and wherein the controller calculates the patient's expiratory flow based on the determined impedance.

44. The breathing assisting device according to claim 42, wherein a linear actuator is configured to move relative to the fixed flow restrictor.

* * * * *